United States Patent
Hirai et al.

(10) Patent No.: US 7,560,428 B2
(45) Date of Patent: Jul. 14, 2009

(54) HAIR GROWTH PROMOTING OLIGOPEPTIDES

(75) Inventors: Yohei Hirai, Yokohama (JP); Kiichiro Nakajima, Kobe (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 50 days.

(21) Appl. No.: 10/557,215

(22) PCT Filed: May 14, 2004

(86) PCT No.: PCT/JP2004/006909

§ 371 (c)(1),
(2), (4) Date: Oct. 31, 2006

(87) PCT Pub. No.: WO2004/101610

PCT Pub. Date: Nov. 25, 2004

(65) Prior Publication Data

US 2008/0051325 A1    Feb. 28, 2008

(51) Int. Cl.
*A61K 38/12* (2006.01)
*A61K 38/18* (2006.01)

(52) U.S. Cl. ........................... 514/9; 530/317
(58) Field of Classification Search ................. None
See application file for complete search history.

(56) References Cited

U.S. PATENT DOCUMENTS

| | | | |
|---|---|---|---|
| 3,755,560 A | 8/1973 | Dickert et al. | |
| 4,254,105 A | 3/1981 | Fukuda | |
| 4,421,769 A | 12/1983 | Dixon et al. | |
| 4,832,946 A * | 5/1989 | Green | 424/115 |
| 4,960,764 A | 10/1990 | Figueroa, Jr. et al. | |
| 5,192,746 A | 3/1993 | Lobl et al. | |
| 5,726,298 A | 3/1998 | Hirai et al. | |
| 7,241,731 B2 * | 7/2007 | Hirai et al. | 514/2 |
| 2003/0086893 A1 | 5/2003 | Hirai et al. | |

FOREIGN PATENT DOCUMENTS

| | | |
|---|---|---|
| EP | 0 200 188 A2 | 11/1986 |
| EP | 0 562 123 A1 | 9/1993 |
| EP | 0 562 123 B1 | 9/1993 |
| EP | 0 698 666 A2 | 2/1996 |
| EP | 0 698 666 B1 | 2/1996 |
| EP | 1 008 603 A1 | 6/2000 |
| EP | 1 008 603 B1 | 6/2000 |
| EP | 1 288 221 A1 | 3/2003 |
| EP | 1 310 511 A2 | 5/2003 |
| JP | 10-147597 A | 6/1998 |
| WO | WO-01/094382 A1 | 12/2001 |

OTHER PUBLICATIONS

Goyal, A. et al. (Jul. 1998). "Characterization of Rat Epimorphin/Syntaxin 2 Expression Suggests a Role in Crypt-Villus Morphogenesis," *Am. J. Physiol.* 275(1 Pt. 1):G114-124.

Hirai, Y. et al. (May 14, 2001). "Epimorphin Mediates Mammary Luminal Morphogenesis through Control of C/EBPβ," *J. Cell Biol* 153(4):785-794.

Koshida, S. et al. (May 19, 1997). "Identification of Cellular Recognition Sequence of Epimorphin and Critical Role of Cell/Epimorphin Interaction in Lung Branching Morphogenesis," *Biochem Biophys. Res. Commun.* 234(2):522-525.

Lehnert, L. et al. (Mar. 5, 2001). "Autocrine Stimulation of Human Pancreatic Duct-Like Development by Soluble Isoforms of Epimorphin In Vitro," *J. Cell Biol* 152(5):911-922.

Matsuki, Y. et al. (Feb. 1995). "Gene Expression of Epimorphin in Rat Incisor Ameloblasts," *Arch. Oral. Biol.* 40(2):161-164.

Mezei, M. (1985). "Liposomes as a Skin Drug Delivery System," *Topics in Pharmaceutical Sciences*. Breimer, D.D. et al., eds. Elsevier Science Publishers B.V.: Amsterdam, The Netherlands, pp. 345-358.

Mori, M. et al. (May 2000). "Factors Affecting Morphogenesis of Rabbit Gallbladder Epithelial Cells Cultured in Collagen Gels," *Cell Tissue Res.* 300(2):331-344.

Oka, Y. et al. (Jan. 10, 1996). "Inductive Influences of Epimorphin on Endothelial in Vitro," *Exp. Cell. Res.* 222(1):189-198.

Supplementary Partial European Search Report mailed on Dec. 21, 2006 for EP Application No. 0473317.6, four pages.

Terasaki, Y. et al. (Aug. 2000), "Increased Expression of Epimorphin in Bleomocyin-Induced Pulmonary Fibrosis in Mice," *Am. J. Respir. Cell Mol. Biol* 23(2):168-174.

Watanabe, S. et al. (Sep. 18, 1998). "A Novel Hepatic Stellate (Ito) Cell-Derived Protein, Epimorphin, Plays a Key Role in the Late Stages of Liver Regeneration," *Biophys. Res. Commun.* 250(2):486-490.

Zhang, L. et al. (Dec. 1998) "Immunohistochemical Distribution of Epimorphin in Human and Mouse Tissues," *Histochem. J.* 30(12):903-908.

* cited by examiner

*Primary Examiner*—Cecilia Tsang
*Assistant Examiner*—Ronald T Niebauer
(74) *Attorney, Agent, or Firm*—Morrison & Foerster LLP

(57) ABSTRACT

The object of the present invention is to provide an oligopeptide having hair growth promoting activity. The present invention provides an oligopeptide which is represented by the formula (I): X1-X2-X3-X4-X5-X6-X7, or the like wherein X1 represents an amino acid residue such as Ser, X2 represents an amino acid residue such as Ile, X3 represents an amino acid residue such as Glu, X4 represents an amino acid residue such as Gln, X5 represents an amino acid residue such as Ser, X6 represents the amino acid residue Cys to which a modifying group containing a carbonyl group binds, or the amino acid residue Lys to which a modifying group containing a carbonyl group binds, and X7 represents an amino acid residue such as Glu or Ala.

9 Claims, 12 Drawing Sheets

HAIR GROWTH PROMOTING OLIGOPEPTIDES

This application is a National Phase filing under 35 U.S.C. 371 of International Application No. PCT/JP20041006909 filed on May 14, 2004, and which claims priority to Japanese Patent Application No. 2003-138567 filed on May 16, 2003, and Japanese Patent Application No. 2003-386185 filed on Nov. 17, 2003, the disclosures of which are incorporated herein by reference in their entirety.

TECHNICAL FIELD

The present invention relates to an oligopeptide having hair growth promoting activity and a medicament comprising the above oligopeptide as an active ingredient.

BACKGROUND ART

The normal morphogenesis of epithelial tissue has been suggested to be controlled by factors derived from mesenchymal cells present around the epithelial tissue. Diseases resulting from the abnormal morphogenesis of epithelial tissue are largely caused by abnormalities of mesenchymal cells. Therefore, an interest has arisen in the clarification of the mechanism in which mesenchymal cells controls the morphogenesis of epithelial tissue. However, substances involved in the control of morphogenesis of epithelial tissue are expressed under time and spatial control in a complicated system, and accordingly, it is extremely difficult to isolate these substances and analyze their functions. It is also difficult to construct a model experimental system simplifying the morphogenesis of epithelial tissue. For these reasons, no significant progress has been made to date in researches in this field. Thus, analysis of the controlling mechanism for the morphogenesis of epithelial tissue has been highly desired in order to elucidate the mechanism of occurrence of diseases associated with the morphogenesis of epithelial tissue and establish methods for treating these diseases.

Under the circumstances, epimorphin involved in the control of the morphogenesis of epithelial tissue was isolated (EP 0562123 (U.S. Pat. No. 5,726,298)). This substance, being a physiologically active substance containing a protein consisting of 277 to 289 amino acids as a core protein, was revealed to be biosynthesized mainly by mesenchymal cells. It was also found that epimorphin had the action of promoting the morphogenesis of epithelial tissue through its action on epithelial cells, and that normal tissue formation was not progressed when epimorphin failed to function.

As to the structure of epimorphin, it has been found that epimorphin molecule can be roughly divided into four fragments from a structural viewpoint (EP 0698666). That is, the polypeptide consisting of full length of epimorphin can be divided into the following four fragments, from its N-terminal, a coiled coil domain (1), a functional domain (2), a coiled coil domain (3), and hydrophobic domain at the C-terminal. In these fragments, it is suggested that the functional domain (the domain specified by 104th to 187th (from N terminal) amino acids in human epimorphin) participates in cell adhesion and is closely related with an expression of physiological activity of epimorphin (EP 0698666).

Since epimorphin has an action for promoting normal morphogenesis, this substance is expected to be useful as an active ingredient of medicaments for preventive or therapeutic treatment of diseases caused by abnormal morphogenesis, or medicaments such as a hair growth promoting agent. However, a native epimorphin obtained from a mammal is almost insoluble in an aqueous media such as saline, which causes difficulty in practically using the substance as medicaments. Some attempts were made to produce new epimorphin derivatives having good solubility while substantially keeping the promoting activity on morphogenesis of the native epimorphin. For example, a modified form (fragment 123) obtained by removing a hydrophobic region at C-terminal has been known (EP 0562123 (U.S. Pat. No. 5,726,298)).

It is also known that a polypeptide having a partial structure of epimorphin promotes morphogenesis of epithelial tissue through its action on epithelial cells (EP 1008603). This peptide is soluble in aqueous media such as saline, and the above publication teaches that this peptide has hair growth promoting activity. In addition, EP 1288221 discloses an oligopeptide having a partial structure of epimorphine, which has hair growth promoting activity.

DISCLOSURE OF THE INVENTION

It is an object of the present invention to provide an oligopeptide having hair growth promoting activity. It is another object of the present invention to provide the aforementioned oligopeptide having high purification efficiency. It is a further object of the present invention to provide a medicament comprising the aforementioned oligopeptide as an active ingredient.

As a result of intensive studies directed towards achieving the aforementioned objects, the present inventors have found that an oligopeptide obtained by modifying the Cys residue or Lys residue in an oligopeptide having a partial structure of epimorphine with a modifying group containing a carbonyl group, has excellent hair growth promoting activity. Moreover, the inventors have also found that an oligopeptide obtained by introducing a linking group into an amino acid sequence contained in an oligopeptide having a partial structure of epimorphine and thus forming a cyclic structure in a molecule thereof, exhibits excellent purification efficiency as well as excellent hair growth promoting activity. The present invention has been completed based on these findings.

That is to say, the present invention provides an oligopeptide, which consists of 5 to 100 amino acid residues comprising the amino acid sequence shown in any one of the following formulas (I) to (IV), and which has hair growth promoting activity, or a modified oligopeptide thereof:

$$X1\text{-}X2\text{-}X3\text{-}X4\text{-}X5\text{-}X6\text{-}X7 \qquad (I);$$

$$X1\text{-}X2\text{-}X3\text{-}X4\text{-}X6\text{-}X5\text{-}X7 \qquad (II);$$

$$X1\text{-}X2\text{-}X3\text{-}X6\text{-}X4\text{-}X5\text{-}X7 \qquad (III); \text{ and}$$

$$X1\text{-}X2\text{-}X6\text{-}X3\text{-}X4\text{-}X5\text{-}X7 \qquad (IV),$$

wherein X1 represents an amino acid residue selected from among Ser, Ala, Tyr, Thr, Pro, Phe, Val, Gly, Leu, Ile, and Met, or it is deleted;

X2 represents an amino acid residue selected from among Ile, Gly, Asn, Thr, Val, Ser, Phe, Leu, Ala, Pro, Cys, and Met, or it is deleted;

X3 represents an amino acid residue selected from among Glu, Lys, Gln, Arg, Ala, Val, Trp, Cys, and Asp;

X4 represents an amino acid residue selected from among Gln, Pro, Glu, Thr, Arg, Ser, His, Cys, and Lys;

X5 represents an amino acid residue selected from among Ser, Trp, Phe, Thr, Cys, Tyr, Pro, Ala, Gly, Val, Leu, Ile, and Met;

X6 represents the amino acid residue Cys to which a modifying group containing a carbonyl group binds, or the amino acid residue Lys to which a modifying group containing a carbonyl group binds; and X7 represents an amino acid residue selected from among Asp, Glu, His, Ser, Ala, Gly, Asn, Tyr, Arg, and Leu, or it is deleted.

Preferably, X1 represents the amino acid residue Ser, X2 represent the amino acid residue Ile, X3 represents the amino acid residue Glu, X4 represents the amino acid residue Gln, X5 represents the amino acid residue Ser, X6 represents the amino acid residue Cys to which a modifying group containing a carbonyl group binds, and X7 represents the amino acid residue Glu or Ala.

There is preferably provided an oligopeptide consisting of 5 to 7 amino acid residues consisting of the amino acid sequence shown in any one of the aforementioned formulas (I) to (IV).

In another aspect, the present invention provides an oligopeptide, which consists of 6 to 100 amino acid residues comprising the amino acid sequence shown in any one of the following formulas (XI) to (XIV), and which has hair growth promoting activity, or a modified oligopeptide thereof:

X1-X2-X3-X4-X5-X6-X7-X8-X9 (XI);

X1-X2-X3-X4-X6-X5-X7-X8-X9 (XII);

X1-X2-X3-X6-X4-X5-X7-X8-X9 (XIII); and

X1-X2-X6-X3-X4-X5-X7-X8-X9 (XIV), wherein X1 represents an amino acid residue selected from among Ser, Ala, Tyr, Thr, Pro, Phe, Val, Gly, Leu, Ile, and Met, or it is deleted;

X2 represents an amino acid residue selected from among Ile, Gly, Asn, Thr, Val, Ser, Phe, Leu, Ala, Pro, Cys, and Met, or it is deleted;

X3 represents an amino acid residue selected from among Glu, Lys, Gln, Arg, Ala, Val, Trp, Cys, and Asp;

X4 represents an amino acid residue selected from among Gln, Pro, Glu, Thr, Arg, Ser, His, Cys, and Lys;

X5 represents an amino acid residue selected from among Ser, Trp, Phe, Thr, Cys, Tyr, Pro, Ala, Gly, Val, Leu, Ile, and Met;

X6 represents the amino acid residue Cys to which a modifying group containing a carbonyl group binds, or the amino acid residue Lys to which a modifying group containing a carbonyl group binds;

X7 represents an amino acid residue selected from among Asp, Glu, His, Ser, Ala, Gly, Asn, Tyr, Arg, and Leu, or it is deleted;

X8 represents the amino acid residue Gln; and

X9 represents an amino acid residue selected from among Asp, Glu, His, Ser, Ala, Gly, Asn, Tyr, Arg, and Leu.

Preferably, at least one of X7 and X9 represents an amino acid residue other than the amino acid residue Asp.

More preferably, X1 represents the amino acid residue Ser, X2 represent the amino acid residue Ile, X3 represents the amino acid residue Glu, X4 represents the amino acid residue Gln, X5 represents the amino acid residue Ser, X6 represents the amino acid residue Cys to which a modifying group containing a carbonyl group binds, X7 represents the amino acid residue Glu or Ala, X8 represents the amino acid residue Gln, and X9 represents the amino acid residue Glu.

There is preferably provided an oligopeptide consisting of 7 to 9 amino acid residues comprising the amino acid sequence shown in any one of the aforementioned formulas (XI) to (XIV).

Preferably, X6 represents the amino acid residue Cys to which a modifying group having a carboxyl group at the terminus thereof binds, or the amino acid residue Lys to which a modifying group having a carboxyl group at the terminus thereof binds.

Preferably, a carbonyl group binds to a hydrocarbon chain containing 2 to 10 carbon atoms in the above modifying group.

Preferably, a carbonyl group binds to a hydrocarbon chain containing 3 to 7 carbon atoms in the above modifying group.

Preferably, the modifying group is derived from N-β-maleimidepropionic acid, N-ϵ-maleimidecaproic acid, or N-κ-maleimideundecanoic acid.

There is preferably provided an oligopeptide shown in any one of the following sequences or a modified oligopeptide thereof:

```
                                          (SEQ ID NO: 1)
    Ser-Ile-Glu-Gln-Ser-Xaa-Ala-Gln-Glu;

(SEQ ID NO: 2)
    Ser-Ile-Glu-Gln-Ser-Xaa-Glu-Gln-Glu;
    and (SEQ ID NO: 3)
    Ser-Ile-Glu-Gln-Ser-Xaa-Glu-Gln-Glu-Ala,
``` wherein Xaa represents the amino acid residue Cys, to which a modifying group derived from N-ϵ-maleimidecaproic acid binds.

In another aspect, the present invention provides a medicament and a hair growth promoting agent, which comprise, as an active ingredient, any of the aforementioned oligopeptides, a modified oligopeptide thereof, or a physiologically acceptable salt thereof.

In a further aspect, the present invention provides: the use of the aforementioned oligopeptide, a modified oligopeptide thereof, or a physiologically acceptable salt thereof, for the production of the aforementioned medicament or hair growth promoting agent; and a method for promoting hair growth, which comprises a step of administering an effective dose of the aforementioned oligopeptide, a modified oligopeptide thereof, or a physiologically acceptable salt thereof, to mammals including humans.

In a further aspect, the present invention provides a cyclic oligopeptide having the amino acid sequence shown in the following formula (1) and having hair growth promoting activity, or a modified oligopeptide thereof:

$$\begin{array}{c} X1\text{—}X2\text{—}X3\text{—}X4\text{—}X5\text{—}X6\text{—}X7\text{—}Y \\ |\underline{\qquad\qquad} \text{L-Cys} \underline{\qquad\qquad}| \end{array} \quad (1)$$

wherein X1 represents an amino acid residue selected from among Ser, Ala, Tyr, Thr, Pro, Phe, Val, Gly, Leu, Ile, and Met, or it is deleted;

X2 represents an amino acid residue selected from among Ile, Gly, Asn, Thr, Val, Ser, Phe, Leu, Ala, Pro, and Met, or it is deleted;

X3 represents an amino acid residue selected from among Glu, Lys, Gln, Arg, Ala, Val, Trp, and Asp;

X4 represents an amino acid residue selected from among Gln, Pro, Glu, Thr, Arg, Ser, His, and Lys;

X5 represents an amino acid residue selected from among Ser, Trp, Phe, Thr, Tyr, Pro, Ala, Gly, Val, Leu, Ile, and Met;

X6 represents the amino acid residue Cys;

X7 represents an amino acid residue selected from among Asp, Glu, His, Ser, Ala, Gly, Asn, Tyr, Arg, and Leu, or it is deleted;

Y is deleted, or represents an amino acid sequence consisting of 1 to 90 amino acid residues; and L represents a linking group.

Preferably, X1 represents the amino acid residue Ser, X2 represent the amino acid residue Ile, X3 represents the amino acid residue Glu, X4 represents the amino acid residue Gln, X5 represents the amino acid residue Ser, X6 represents the amino acid residue Cys, and X7 represents the amino acid residue Glu or Ala.

Preferably, Y is deleted, or represents an amino acid sequence consisting of 1 to 12 amino acid residues.

There is preferably provided a cyclic oligopeptide having the amino acid sequence shown in the following formula (2) and having hair growth promoting activity, or a modified oligopeptide thereof:

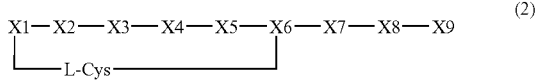

(2)

wherein X1 represents an amino acid residue selected from among Ser, Ala, Tyr, Thr, Pro, Phe, Val, Gly, Leu, Ile, and Met, or it is deleted;

X2 represents an amino acid residue selected from among Ile, Gly, Asn, Thr, Val, Ser, Phe, Leu, Ala, Pro, and Met, or it is deleted;

X3 represents an amino acid residue selected from among Glu, Lys, Gln, Arg, Ala, Val, Trp, and Asp;

X4 represents an amino acid residue selected from among Gln, Pro, Glu, Thr, Arg, Ser, His, and Lys;

X5 represents an amino acid residue selected from among Ser, Trp, Phe, Thr, Tyr, Pro, Ala, Gly, Val, Leu, Ile, and Met;

X6 represents the amino acid residue Cys;

X7 represents an amino acid residue selected from among Asp, Glu, His, Ser, Ala, Gly, Asn, Tyr, Arg, and Leu, or it is deleted;

X8 represents the amino acid residue Gln;

X9 represents an amino acid residue selected from among Asp, Glu, His, Ser, Ala, Gly, Asn, Tyr, Arg, and Leu; and L represents a linking group.

Preferably, at least one of X7 and X9 represents an amino acid residue other than the amino acid residue Asp.

Preferably, X1 represents the amino acid residue Ser, X2 represent the amino acid residue Ile, X3 represents the amino acid residue Glu, X4 represents the amino acid residue Gln, X5 represents the amino acid residue Ser, X6 represents the amino acid residue Cys, X7 represents the amino acid residue Glu or Ala, X8 represents the amino acid residue Gln, and X9 represents the amino acid residue Glu.

In another aspect, the present invention provides a cyclic oligopeptide having the amino acid sequence shown in the following formula (3) and having hair growth promoting activity, or a modified oligopeptide thereof:

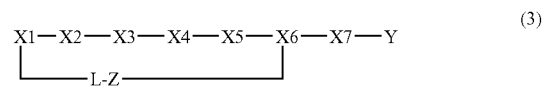

(3)

wherein X1 represents an amino acid residue selected from among Ser, Ala, Tyr, Thr, Pro, Phe, Val, Gly, Leu, Ile, and Met, or it is deleted;

X2 represents an amino acid residue selected from among Ile, Gly, Asn, Thr, Val, Ser, Phe, Leu, Ala, Pro, and Met, or it is deleted;

X3 represents an amino acid residue selected from among Glu, Gln, Arg, Ala, Val, Trp, and Asp;

X4 represents an amino acid residue selected from among Gln, Pro, Glu, Thr, Arg, Ser, and His;

X5 represents an amino acid residue selected from among Ser, Trp, Phe, Thr, Tyr, Pro, Ala, Gly, Val, Leu, Ile, and Met;

X6 represents the amino acid residue Lys;

X7 represents an amino acid residue selected from among Asp, Glu, His, Ser, Ala, Gly, Asn, Tyr, Arg, and Leu, or it is deleted;

Y is deleted, or represents an amino acid sequence consisting of 1 to 90 amino acid residues;

L represents a linking group; and

Z represents a group capable of reacting with Lys and binding thereto.

Preferably, X1 represents the amino acid residue Ser, X2 represent the amino acid residue Ile, X3 represents the amino acid residue Glu, X4 represents the amino acid residue Gln, X5 represents the amino acid residue Ser, X6 represents the amino acid residue Cys, and X7 represents the amino acid residue Glu or Ala.

Preferably, Y is deleted, or represents an amino acid sequence consisting of 1 to 12 amino acid residues.

There is preferably provided a cyclic oligopeptide having the amino acid sequence shown in the following formula (4) and having hair growth promoting activity, or a modified oligopeptide thereof:

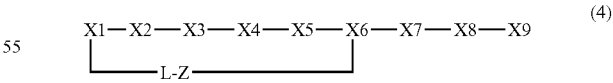

(4)

wherein X1 represents an amino acid residue selected from among Ser, Ala, Tyr, Thr, Pro, Phe, Val, Gly, Leu, Ile, and Met, or it is deleted;

X2 represents an amino acid residue selected from among Ile, Gly, Asn, Thr, Val, Ser, Phe, Leu, Ala, Pro, and Met, or it is deleted;

X3 represents an amino acid residue selected from among Glu, Gln, Arg, Ala, Val, Trp, and Asp;

X4 represents an amino acid residue selected from among Gln, Pro, Glu, Thr, Arg, Ser, and His;

X5 represents an amino acid residue selected from among Ser, Trp, Phe, Thr, Tyr, Pro, Ala, Gly, Val, Leu, Ile, and Met;

X6 represents the amino acid residue Lys;

X7 represents an amino acid residue selected from among Asp, Glu, His, Ser, Ala, Gly, Asn, Tyr, Arg, and Leu, or it is deleted;

X8 represents the amino acid residue Gln;

X9 represents an amino acid residue selected from among Asp, Glu, His, Ser, Ala, Gly, Asn, Tyr, Arg, and Leu;

L represents a linking group; and

Z represents a group capable of reacting with Lys and binding thereto.

Preferably, at least one of X7 and X9 represents an amino acid residue other than the amino acid residue Asp.

Preferably, X1 represents the amino acid residue Ser, X2 represent the amino acid residue Ile, X3 represents the amino acid residue Glu, X4 represents the amino acid residue Gln, X5 represents the amino acid residue Ser, X6 represents the amino acid residue Cys, X7 represents the amino acid residue Glu or Ala, X8 represents the amino acid residue Gln, and X9 represents the amino acid residue Glu.

Preferably, the linking group L contains 6 to 8 carbon atoms.

Preferably, a carbonyl group binds to a hydrocarbon chain containing 5 to 7 carbon atoms in the linking group L.

Preferably, the linking group L is —CO—(CH$_2$)$_n$—NH— wherein n represents an integer between 5 and 7.

Preferably, —CO in the linking group L binds to X1, and NH— in the linking group L binds to the Cys residue binding to X6 or to a group represented by Z.

Particularly preferably, there is provided a cyclic oligopeptide shown in any one of the following sequences, or a modified oligopeptide thereof:

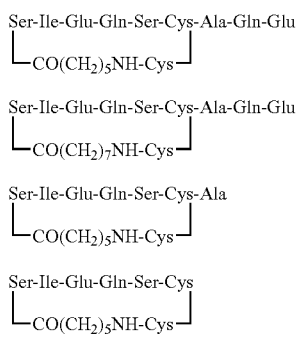

In a further aspect, the present invention provides a medicament and a hair growth promoting agent, which comprise, as an active ingredient, any of the aforementioned cyclic oligopeptides, a modified oligopeptide thereof, or a physiologically acceptable salt thereof.

In a further aspect, the present invention provides a hair growth promoting agent, which comprises, as active ingredients, any of the aforementioned cyclic oligopeptides, a modified oligopeptide thereof, or a physiologically acceptable salt thereof, and minoxidil.

In a further aspect, the present invention provides: the use of the aforementioned cyclic oligopeptide, a modified oligopeptide thereof, or a physiologically acceptable salt thereof, for the production of the aforementioned medicament or hair growth promoting agent; and a method for promoting hair growth, which comprises a step of administering an effective dose of the aforementioned cyclic oligopeptide, a modified oligopeptide thereof, or a physiologically acceptable salt thereof, to mammals including humans.

BRIEF DESCRIPTION OF THE DRAWINGS

FIG. 1A is left view; FIG. 1*b* is right view;

FIG. 2A is left view; FIG. 2B is right view;

FIG. 3A is left view; FIG. 3B is right view;

FIG. 10A is activity; FIG. 10B is the reverse phase purified product;

BEST MODE FOR CARRYING OUT THE INVENTION

Figures 1A, 1B:
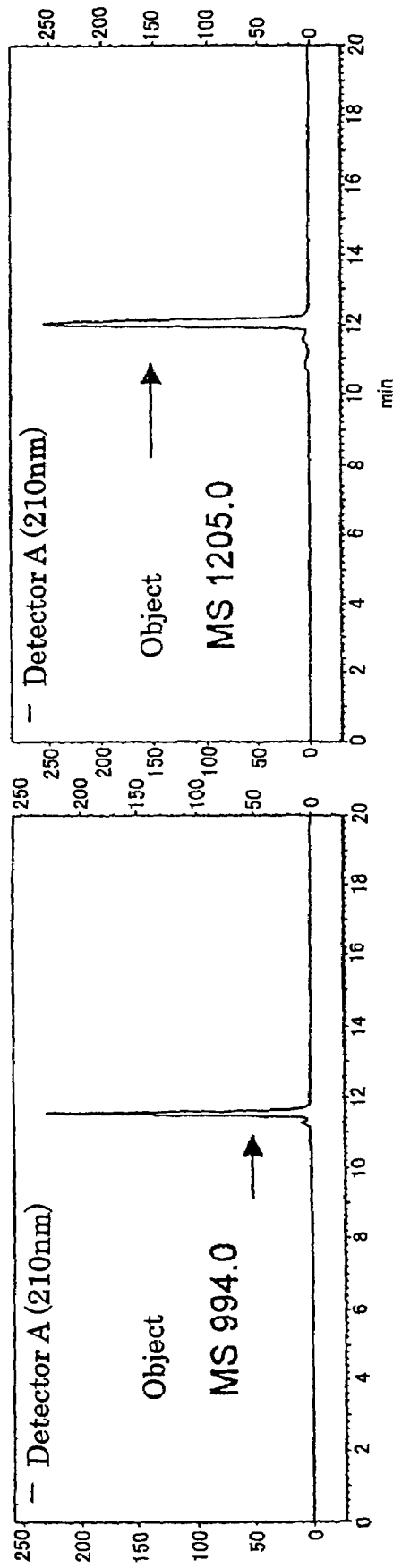
FIGS. 1A-1B show the results obtained by analyzing the synthesized oligopeptide and a reaction product thereof with a modifying reagent by liquid chromatography.

The embodiments of the present invention will be described in detail below.

The first embodiment of the oligopeptides of the present invention is an oligopeptide, which consists of 5 to 100 amino acid residues comprising the amino acid sequence shown in any one of the following formulas (I) to (IV), and which has hair growth promoting activity:

X1-X2-X3-X4-X5-X6-X7    (I);

X1-X2-X3-X4-X6-X5-X7    (II);

X1-X2-X3-X6-X4-X5-X7    (III); and

X1-X2-X6-X3-X4-X5-X7    (IV), wherein X1 represents an amino acid residue selected from among Ser, Ala, Tyr, Thr, Pro, Phe, Val, Gly, Leu, Ile, and Met, or it is deleted;

X2 represents an amino acid residue selected from among Ile, Gly, Asn, Thr, Val, Ser, Phe, Leu, Ala, Pro, Cys, and Met, or it is deleted;

X3 represents an amino acid residue selected from among Glu, Lys, Gln, Arg, Ala, Val, Trp, Cys, and Asp;

X4 represents an amino acid residue selected from among Gln, Pro, Glu, Thr, Arg, Ser, His, Cys, and Lys;

X5 represents an amino acid residue selected from among Ser, Trp, Phe, Thr, Cys, Tyr, Pro, Ala, Gly, Val, Leu, Ile, and Met;

X6 represents the amino acid residue Cys to which a modifying group containing a carbonyl group binds, or the amino acid residue Lys to which a modifying group containing a carbonyl group binds; and X7 represents an amino acid residue selected from among Asp, Glu, His, Ser, Ala, Gly, Asn, Tyr, Arg, and Leu, or it is deleted.

The second embodiment of the oligopeptides of the present invention is an oligopeptide, which consists of 6 to 100 amino acid residues comprising the amino acid sequence shown in any one of the following formulas (XI) to (XIV), and which has hair growth promoting activity:

$$X1\text{-}X2\text{-}X3\text{-}X4\text{-}X5\text{-}X6\text{-}X7\text{-}X8\text{-}X9 \quad (XI);$$

$$X1\text{-}X2\text{-}X3\text{-}X4\text{-}X6\text{-}X5\text{-}X7\text{-}X8\text{-}X9 \quad (XII);$$

$$X1\text{-}X2\text{-}X3\text{-}X6\text{-}X4\text{-}X5\text{-}X7\text{-}X8\text{-}X9 \quad (XIII); \text{ and}$$

$$X1\text{-}X2\text{-}X6\text{-}X3\text{-}X4\text{-}X5\text{-}X7\text{-}X8\text{-}X9 \quad (XIV),$$

wherein X1 to X7 represents an amino acid residue as defined above; X8 represents the amino acid residue Gln; and X9 represents an amino acid residue selected from among Asp, Glu, His, Ser, Ala, Gly, Asn, Tyr, Arg, and Leu.

In the present invention, it is preferable that at least one of X7 and X9 represent an amino acid residue other than the amino acid residue Asp. This is because when at least one of X7 and X9 is an amino acid residue other than the amino acid residue Asp, β transition (succinimide) caused by asparatic acid that may be generated when both X7 and X9 are the amino acid residues Asp, does not take place, and because the synthesis yield can thereby be improved. It is more preferable that X7 be an amino acid residue other than the amino acid residue Asp. This is because when X7 is Asp, such β transition often takes place.

Each of the aforementioned amino acid sequences (I) to (IV) and (XI) to (XIV) is based on an amino acid sequence comprising a deletion of one amino acid residue (Lys) at the N-terminus and two amino acid residues (Asp-Glu) at the C-terminus, or an amino acid sequence obtained by further changing the position of the cysteine residue (Cys) in the above amino acid sequence, wherein the above Cys residue is substituted with the amino acid residue Cys to which a modifying group containing a carbonyl group binds, or with the amino acid residue Lys to which a modifying group containing a carbonyl group binds, with respect to the amino acid sequence consisting of 11 amino acid residues from the C-terminus of the polypeptide (II) disclosed in EP 1008603. Moreover, each of the aforementioned amino acid sequences further comprises a deletion, substitution, and/or addition of one or several amino acids, based on the aforementioned amino acid sequence. Oligopeptides comprising the aforementioned amino acid sequences (I) to (IV) and (XI) to (XIV) have excellent hair growth promoting activity, as specifically described later in the examples.

In the amino acid sequences (I) to (IV) and (XI) to (XIV), X6 represents the amino acid residue Cys to which a modifying group containing a carbonyl group binds, or the amino acid residue Lys to which a modifying group containing a carbonyl group binds.

In a preferred embodiment of the present invention, a modifying group has a carboxyl group at the terminus thereof. In addition, in a more preferred embodiment of the present invention, a carbonyl group binds to a hydrocarbon chain containing 2 to 10 carbon atoms, and more preferably 3 to 7 carbon atoms, in such a modifying group.

In the present invention, when X6 represents the amino acid residue Cys to which a modifying group containing a carbonyl group binds, preferred examples of such a modifying group may include: a modifying group derived from N-β-maleimidepropionic acid; a modifying group derived from N-ε-maleimidecaproic acid; and a modifying group derived from N-κ-maleimideundecanoic acid. Such a modifying group can be introduced into a cysteine residue in an oligonucleotide by allowing a reagent such as N-β-maleimidepropionic acid, N-ε-maleimidecaproic acid, or N-κ-maleimideundecanoic acid to react with the oligonucleotide, so as to allow a sulfhydryl group in the cysteine residue in the oligonucleotide to react with the above reagent.

Moreover, in the present invention, when X6 represents the amino acid residue Lys to which a modifying group containing a carbonyl group binds, specific examples of such a modifying group are the same as those in the aforementioned case where X6 represents the amino acid residue Cys to which a modifying group containing a carbonyl group binds.

The oligopeptide of the present invention consists of 5 to 100 amino acid residues comprising an amino acid sequence shown in any one of the formulas (I) to (IV) or (XI) to (XIV). For example, the lower limit of the number of amino acid residues is any one selected from among 5, 6, 7, 8, 9, 10, 11, 12, 13, 14, and 15. The upper limit thereof is any one selected from among 15, 20, 25, 30, 35, 40, 45, 50, 60, 70, 80, 90, and 100. The number of amino acid residues is preferably between 5 and 40, more preferably between 6 and 30, further more preferably between 7 and 20, further more preferably between 7 and 15, further more preferably between 7 and 12, and particularly preferably between 7 and 10. The number of amino acid residues is preferably selected such that the oligopeptide is soluble in an aqueous medium such as a normal saline solution or water and such that it has biological activity.

The third embodiment of the oligopeptides of the present invention is a cyclic oligopeptide having the amino acid sequence shown in the following formula (1) and having hair growth promoting activity, or a modified peptide thereof:

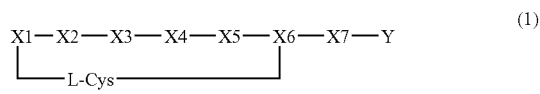

(1)

wherein X1 represents an amino acid residue selected from among Ser, Ala, Tyr, Thr, Pro, Phe, Val, Gly, Leu, Ile, and Met, or it is deleted;

X2 represents an amino acid residue selected from among Ile, Gly, Asn, Thr, Val, Ser, Phe, Leu, Ala, Pro, and Met, or it is deleted;

X3 represents an amino acid residue selected from among Glu, Lys, Gln, Arg, Ala, Val, Trp, and Asp;

X4 represents an amino acid residue selected from among Gln, Pro, Glu, Thr, Arg, Ser, His, and Lys;

X5 represents an amino acid residue selected from among Ser, Trp, Phe, Thr, Tyr, Pro, Ala, Gly, Val, Leu, Ile, and Met;

X6 represents the amino acid residue Cys;

X7 represents an amino acid residue selected from among Asp, Glu, His, Ser, Ala, Gly, Asn, Tyr, Arg, and Leu, or it is deleted;

Y is deleted, or represents an amino acid sequence consisting of 1 to 90 amino acid residues; and L represents a linking group.

Preferred examples of the aforementioned oligopeptide include a cyclic oligopeptide having the amino acid sequence shown in the following formula (2) and having hair growth promoting activity, or a modified peptide thereof:

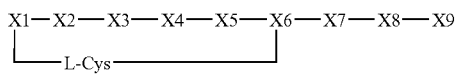
(2)

wherein X1 to X7 and L are the same as defined in the formula (1);

X8 represents the amino acid residue Gln; and

X9 represents an amino acid residue selected from among Asp, Glu, His, Ser, Ala, Gly, Asn, Tyr, Arg, and Leu.

The fourth embodiment of the oligopeptides of the present invention is a cyclic oligopeptide having the amino acid sequence shown in the following formula (3) and having hair growth promoting activity, or a modified peptide thereof:

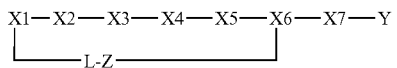
(3)

wherein X1 represents an amino acid residue selected from among Ser, Ala, Tyr, Thr, Pro, Phe, Val, Gly, Leu, Ile, and Met, or it is deleted;

X2 represents an amino acid residue selected from among Ile, Gly, Asn, Thr, Val, Ser, Phe, Leu, Ala, Pro, and Met, or it is deleted;

X3 represents an amino acid residue selected from among Glu, Gln, Arg, Ala, Val, Trp, and Asp;

X4 represents an amino acid residue selected from among Gln, Pro, Glu, Thr, Arg, Ser, and His;

X5 represents an amino acid residue selected from among Ser, Trp, Phe, Thr, Tyr, Pro, Ala, Gly, Val, Leu, Ile, and Met;

X6 represents the amino acid residue Lys;

X7 represents an amino acid residue selected from among Asp, Glu, His, Ser, Ala, Gly, Asn, Tyr, Arg, and Leu, or it is deleted;

Y is deleted, or represents an amino acid sequence consisting of 1 to 90 amino acid residues;

L represents a linking group; and

Z represents a group capable of reacting with Lys and binding thereto.

Preferred examples of the aforementioned oligopeptide include a cyclic oligopeptide having the amino acid sequence shown in the following formula (4) and having hair growth promoting activity, or a modified peptide thereof:

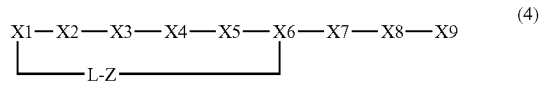
(4)

wherein X1 to X7, L and Z are the same as defined in the formula (3);

X8 represents the amino acid residue Gln; and

X9 represents an amino acid residue selected from among Asp, Glu, His, Ser, Ala, Gly, Asn, Tyr, Arg, and Leu.

In the present invention, it is preferable that at least one of X7 and X9 represent an amino acid residue other than the amino acid residue Asp. This is because when at least one of X7 and X9 is an amino acid residue other than the amino acid residue Asp, β transition (succinimide) caused by asparatic acid that may be generated when both X7 and X9 are the amino acid residues Asp, does not take place, and because the synthesis yield can thereby be improved. It is more preferable that X7 be an amino acid residue other than the amino acid residue Asp. This is because when X7 is Asp, such β transition often takes place.

Each of the aforementioned amino acid sequences is based on an amino acid sequence comprising a deletion of one amino acid residue (Lys) at the N-terminus and two amino acid residues (Asp-Glu) at the C-terminus with respect to the amino acid sequence consisting of 11 amino acid residues from the C-terminus of the polypeptide (II) disclosed in EP 1008603.

As specifically described in the examples below, the aforementioned cyclic oligopeptide of the present invention is able to exhibit excellent hair growth promoting activity, even after it has been treated with 30% acetonitrile and 0.1% trifluoroacetic acid and then dried. Such a treatment with 30% acetonitrile and 0.1% trifluoroacetic acid may be the same condition as that for purifying an oligopeptide by reverse phase chromatography. Thus, the cyclic oligopeptide of the present invention can be purified by reverse phase chromatography, thereby increasing purification efficiency.

In the amino acid sequences (1) to (4), X6 represents the amino acid residue Cys or Lys, and particularly preferably X6 represents the amino acid residue Cys.

The cyclic oligopeptide of the present invention is characterized in that X1 binds to X6 via -L-Cys- (wherein L represents a linking group binding to X1, and Cys represents the residue Cys binding to X6) or -L-Z (wherein L represents a linking group binding to X1, and Z represents a group capable of reacting with Lys and binding thereto), so as to form an intramolecular cyclic structure. Specific examples of such a group represented by Z that is capable of reacting with Lys and binding thereto may include an N-hydroxysuccimide ester group, an imide ester group, and a hydroxymethylphosphine group.

Specific examples of a linking group represented by L may include linking groups containing 6 to 8 carbon atoms, such as a linking group wherein a carbonyl group binds to a hydrocarbon chain containing 5 to 7 carbon atoms. A specific example of such a linking group L may be —CO—(CH$_2$)$_n$—NH— (wherein n represents an integer between 5 and 7). In the aforementioned linking group L, —CO binds to X1, and NH— is able to bind to the residue Cys binding to X6, or is able to bind to Z.

The cyclic oligopeptide of the present invention consists of 5 to 98 amino acid residues having the amino acid sequence shown in formula (1) or (3). The number of amino acid residues is preferably between 5 and 20, more preferably between 7 and 15, further more preferably between 7 and 12, and particularly preferably between 7 and 10. The number of amino acid residues is preferably selected such that the oligopeptide is soluble in an aqueous medium such as a normal saline solution or water and such that it has biological activity.

Hereafter, all of the aforementioned oligopeptides in the first to fourth embodiments (namely, an oligopeptide consisting of 5 to 100 amino acid residues comprising the amino acid sequence shown in any one of formulas (I) to (IV) and having hair growth promoting activity; an oligopeptide consisting of 5 to 100 amino acid residues comprising the amino acid sequence shown in any one of formulas (XI) to (XIV) and having hair growth promoting activity; a cyclic oligopeptide having the amino acid sequence shown in formula (1) and having hair growth promoting activity; and a cyclic oligopeptide having the amino acid sequence shown in formula (3) and having hair growth promoting activity) are referred to as the oligopeptide of the present invention.

The type of amino acid residue in the oligopeptide of the present invention is not particularly limited, and may be any of natural type amino acid residue, non-natural type amino acid residue, or derivatives thereof. The amino acid may be L-amino acid, D-amino acid or a mixture thereof. The type of the amino acid may be any of α-amino acid, β-amino acid, γ-amino acid or δ-amino acid. α-amino acid, which is a natural type amino acid, is preferred.

The non-natural type amino acid used herein covers all of the amino acids other than 20 types of the natural type amino acids which constitute a natural protein (glycine, L-alanine, L-valine, L-leucine, L-isoleucine, L-serine, L-threonine, L-aspartic acid, L-glutamic acid, L-asparagine, L-glutamine, L-lysine, L-arginine, L-cysteine, L-methionine, L-phenylalanine, L-tyrosine, L-tryptophan, L-histidine, L-proline). Specific examples include (1) non-natural type amino acid wherein an atom in a natural type amino acid is substituted with another substance, (2) an optical isomer as to a side chain of natural type amino acid, (3) non-natural type amino acid obtained by introducing a substituent into a side chain of natural type amino acid, and (4) non-natural type amino acid obtained by substituting the side chain of natural type amino acid to alter hydrophobic property, reactivity, charge, size of the molecule, hydrogen bonding ability and the like.

Another embodiment of the present invention is a modified oligopeptide of the oligopeptide which consists of 5 to 100 amino acid residues comprising the amino acid sequence shown in the aforementioned amino acid sequences (I) to (IV) or (XI) to (XIV), and which has hair growth promoting activity which is similar with that of the aforementioned oligopeptide of the present invention.

Further another embodiment of the present invention is a modified oligopeptide of the oligopeptide which consists of 7 to 98 amino acid residues comprising any of the amino acid sequence shown in the aforementioned amino acid sequences (1) to (4), and which has hair growth promoting activity which is similar with that of the aforementioned oligopeptide of the present invention.

One of ordinary skill in the art can easily ascertain that the oligopeptides of the present invention or the modified oligopeptides have a hair growth promoting activity by test methods, such as the one described in detail in the Examples of the present specification or alterations or modifications to said test method. Examples of such test methods disclosed herein include but are not limited to the below.

(1) C3H and C57BL/6 mice are known to have sustained telogen for about 50 days from the 45th day after the birth to around the 95th day. Their hair cycle is easily judged based on the skin color changes, i.e., from pink in telogen to gray or black in anagen. A hair growth promoting activity can be evaluated by using this mice and evaluating whether or not the administration the test substance promotes the transition from telogen to anagen.

(2) A hair growth promoting activity can be evaluated by using a monoclonal antibody (for example, a monoclonal antibody produced by the hybridoma having an accession number FERM BP-8121) which specifically recognizes an antigen present in epithelial new follicles (for example, about 220 kD antigen), or a fragment thereof. Specifically, skin tissue from an organism is cultured in the presence of a test substance, and the skin tissue is collected, and reacted with the aforementioned monoclonal antibody or a fragment thereof. A hair growth promoting activity can be evaluated by detecting or measuring the monoclonal antibody or a fragment thereof which reacted with the skin tissue, and thereby measuring the amount of the antigen expressed on epithelial new follicles. Also, the skin is cut and cultured in the presence of a test substance, and the protein in the culture is reacted with the aforementioned monoclonal antibody, thereby a hair growth promoting activity can be evaluated.

The term "modified" in the modified oligopeptide of the present invention must be construed in the broadest sense including chemical modification and biological modification. Examples of the modification include introduction of a functional group such as alkylation, esterification, halogenation, and amination, or conversion of a functional group such as oxidation, reduction, addition, and elimination, or introduction of a sugar compound (a monosaccharide, disaccharide, oligosaccharide, or polysaccharide) or a lipid compound, phosphorylation, and biotinylation. However, the modifications are not limited to these examples.

An example of the preferred modified oligopeptide includes a biotinylated oligopeptide, and a more preferred example includes an oligopeptide of which N-terminal is bound by biotin with or without a spacer. In the above modified oligopeptide, an appropriate chemical modification may be added to the biotin as long as the desirable physiological activity is maintained. In order to introduce biotin to the N-terminal of the oligopeptide by means of a spacer having an appropriate length, for example, NHS-Biotin or NHS-LC-Biotin (available from Pierce) can be used.

The above various oligopeptides of the present invention (including modified oligopeptides) may be in free form, or may be provided as acid addition salts or base addition salts. Examples of the acid addition salts include mineral acid salts such as hydrochloride, sulfate, nitrate, and phosphate; organic acid salts such as para-toluenesulfonate, methanesulfonate, citrate, oxalate, maleate, and tartrate. Examples of the base addition salts include metal salts such as sodium salt, a potassium salt, a calcium salt, and a magnesium salt; an ammonium salt; organic ammonium salts such as a methyl ammonium salt, and a trimethyl ammonium salt. The oligopeptide may form a salt with amino acids such as glycine, or may form a counter ion in the molecule.

Further, these oligopeptides or salts thereof may exist in a form of a hydrate or a solvate. The above oligopeptides have plural asymmetric carbon atoms. Although the stereochemistry of each asymmetric carbon atoms is not limited, it is preferable that the amino acid reside is L-amino acid. Stereoisomers such as optical isomers or diastereomers based on the asymmetric carbon atoms, any mixtures of the stereoisomers, and racemates fall within the scope of the present invention.

The oligopeptide of the present invention can be synthesized by a conventional chemical technique for peptide synthesis, such as solid phase or liquid phase method. There are various kinds of articles about protective group for amino group or the like and condensation agent for a condensation reaction in the filed of peptide synthesis, and accordingly, these articles can be referred to for the synthesis. In the solid phase method, commercially available various peptide synthesizers can be utilized. The synthesis can be efficiently carried out by performing protection and deprotection of functional groups as necessary. As for a method for introducing and removing a protective group, for example, Protective Groups in Organic Synthesis, T. W. Greene, John Wiley & Sons, Inc. 1981 and the like can be referred to. Methods for producing modified oligopeptides including chemical modification and biological modification are well known to one of ordinary skill in the art, and any methods can be used.

By applying an ordinary biological method such as a gene expression procedure, a desired oligopeptide can be obtained by constructing a recombinant vector containing a DNA sequence encoding the above oligopeptide, preparing a microorganism (transformant) transformed by the vector, and separating and purifying the oligopeptide from culture of the transformant. The method for producing the oligopeptides is not limited to these chemical and biological methods. Methods for producing modified oligopeptides including chemical modification and biological modification are well known to one of ordinary skill in the art, and any methods can be used.

Next, a method for producing the oligopeptide of the present invention, which is a cyclic oligopeptide, will be specifically described. The cyclic oligopeptide of the present invention can be synthesized by the following procedures (1) to (3):

(1) First, $HOOC-(CH_2)_n-NH_2$ (wherein n represents an integer between 5 and 7) that is a compound corresponding to the linking group L ($-CO-(CH_2)_n-NH-$) is chemically synthesized.

(2) Subsequently, an oligopeptide represented by Cys-L-X1-X2-X3-X4-X5-X6-X7 (in a case where X6 is Cys) or Z-L-X1-X2-X3-X4-X5-X6-X7 (in a case where X6 is Lys) is synthesized by the aforementioned common peptide synthesis method. For example, using a commercially available peptide automatic synthesizer (e.g. a peptide automatic synthesizer 430A model manufactured by Applied Biosystems, etc.), peptide chains are successively extended from the C-terminus in accordance with the program thereof by the BOC method, so as to synthesize a protective resin for peptides of interest.

(3) Finally, when X6 is Cys, the residue Cys at the N-terminus is allowed to bind to Cys represented by X6 via a covalent bond. Such a covalent bond can be formed by common methods. Specifically, an oligopeptide having a free thiol group is subjected to iodine oxidation in an acetic acid solution, so as to conduct a cyclization reaction, thereby forming the aforementioned covalent bond.

Moreover, when X6 is Lys, the residue Z at the N-terminus is allowed to bind to Lys represented by X6 via a covalent bond. Such a covalent bond can be formed by common methods.

The oligopeptide of the present invention is useful as an active ingredient for a medicament. The term "medicament" is used in the present specification to have the broadest sense, which includes not only a medicament used for prevention or treatment of the diseases of mammals including humans, but also a hair growth promoting agent that may be classified as a quasi drug or cosmetic in some cases.

Specific examples of a target to which the medicament of the present invention is administered, beneficial effects thereof, and target diseases that are treated with the medicament of the present invention, are given below.

(1) The oligopeptide of the present invention shows revascularization effect, regeneration promoting effect, cardiovascular regeneration effect, inductive effect on vascular endothelial cell, and the like, and is useful for the therapy and prevention of chronic obstructive arteriosclerosis, Buerger's disease, sever angina pectoris, arteriosclerosis and the like (Exp Cell Res 1996 Jan. 10, 222(1):189-98).

(2) The oligopeptide of the present invention is involved in morphogenesis of pancreatic endothelium, and is useful for the therapy and prevention of diabetes and the like (J Cell Biol 2001, March 5; 152(5):911-22).

(3) The oligopeptide of the present invention is involved in formation (regeneration) of liver, and is useful for the therapy and prevention of liver metabolism failure (Biochem Biophys Res Commun 1998 Sep. 18; 250(2):486-90).

(4) The oligopeptide of the present invention is involved in formation of bone and tooth, and is useful for the therapy and prevention of periodontics, fracture, bone tumor, bone deficiency, and osteoporosis (Arch Oral Biol 1995 February; 40(2):161-4).

(5) The oligopeptide of the present invention is involved in lung branching morphogenesis and pulmonary fibrosis, and is useful for the therapy and prevention of lung diseases (Biochem Biophys Res Commun 1997 May 19; 234(2):522-5; and Am J Respir Cell Mol Biol 2000 August; 23(2):168-74).

(6) The oligopeptide of the present invention is involved in crypt-villus morphogenesis, and is useful for the therapy and prevention of intestine diseases (Am J Physiol 1998 July; 275(1 Pt1):G114-24).

(7) The oligopeptide of the present invention is involved in maintenance of muscle structure, and is useful for the therapy and prevention of muscular dystrophy and the like (Histochem J 1998 December; 30(12):903-8).

(8) The oligopeptide of the present invention is involved in morphogenesis of gallbladder epithelium, and is useful for the therapy and prevention of gallbladder diseases (Cell Tissue Res 2000 May; 300(2):331-44).

(9) The oligopeptide of the present invention is involved in mammary luminal morphogenesis, and is useful for the therapy and prevention of mammary diseases (J Cell Biol 2001 May 14; 153(4):785-94).

Most preferably among these, the oligopeptide of the present invention can be used as a hair growth promoting agent.

The term "hair growth promoting agent" used in the present specification should be interpreted in the broadest sense, which includes hair growth promotion, promotion of trichogenous function, and prevention of alopecia. The above term must not be interpreted in a limited sense in all cases.

Moreover, when the cyclic oligopeptide of the present invention, a modified oligopeptide thereof, or a physiologically acceptable salt thereof, is used as a hair growth promoting agent, it can also be used with the combination of minoxidil.

As a medicament of the invention, one or more oligopeptides selected from among the oligopeptides mentioned above or their physiologically acceptable salt, may be used. Generally, however, it is preferable to prepare and administer a pharmaceutical composition comprising one or more of the above oligopeptides as an active ingredient by using one or more pharmaceutically acceptable pharmaceutical additives. A hair growth promoting agent containing one or more of the aforementioned oligopeptides as an active ingredient can be applied in a form of external preparations such as a cream, a spray, a coating solution, and a patch. The agent can be administered to a target site directly in a form of an injection. It is possible to provide the agent in any form suitable for the purpose of use as a hair growth promoting agent.

For example, the above oligopeptides as an active ingredient may be added to a shampoo or a rinse, or the above oligopeptide can be encapsulated into a liposome to manufacture a preparation. The composition in the aforementioned forms also falls within the medicament of the present invention. In order to achieve an effective transdermal absorption of the oligopeptides of the invention through the keratin layer of skin, it is preferable to add an appropriate detergent, lipid-soluble substance of the like in a cream.

For topical administration in mammals, the composition of the present invention may be provided as a wide variety of product types including, but are not limited to, lotions, creams, gels, sticks, sprays, ointments and pastes. These product types may comprise several types of formulations including, but not limited to solutions, emulsions, gels, solids, and liposomes.

Compositions useful for topical administration of the compositions of the present invention formulated as solutions typically include a pharmaceutically-acceptable aqueous or organic solvent. The terms "pharmaceutically-acceptable organic solvent" refer to a solvent which is capable of having an oligopeptide of the present invention dispersed or dissolved therein, and of possessing acceptable safety properties (e.g., irritation and sensitization characteristics). Examples of suitable organic solvents include: propylene glycol, polyethylene glycol (200-600), polypropylene glycol (425-2025), glycerol, 1,2,4-butanetriol, sorbitol esters, 1,2,6-hexanetriol, ethanol, isopropanol, butanediol, and mixture thereof.

If the topical composition is formulated as an aerosol and applied to the skin as a spray-on, a propellant is added to a solution composition. Examples of propellants useful herein include, but are not limited to, the chlorinated, fluorinated or chloro-fluorinated lower molecular weight hydrocarbons.

The topical composition may be formulated as a solution comprising an emollient. As used herein, "emollients" refer to materials used for the prevention or relief of dryness, as well as for the protection of the skin. A wide variety of suitable emollients are known and may be used in the present invention.

Another type of product that may be formulated from a composition comprising an oligopeptide of the present invention is a cream and a lotion.

Yet another type of product that may be formulated from a composition comprising an oligopeptide of the present invention is an ointment. An ointment may comprise a simple base of animal or vegetable oils or semi-solid hydrocarbons (oleaginous). Ointments may also comprise absorption ointment bases which absorb water to form emulsions. Ointments carriers may also be water soluble.

Another type of formulation is an emulsion. Emulsifiers may be nonionic, anionic or cationic, and examples of emulsifiers are described in, for example, U.S. Pat. Nos. 3,755,560 and 4,421,769.

Lotions and creams can be formulated as emulsion or solution. Single emulsions for topical preparations, such as lotions and creams, of the oil-in-water type and water-in-oil type are well-known in the art. Multiphase emulsion compositions, such as the water-in-oil-in-water type, are also known, as disclosed, for example, in U.S. Pat. No. 4,254,105. Triple emulsions are also useful for topical administration of the present invention and comprise an oil-in-water-in-silicone fluid emulsion as disclosed, for example in U.S. Pat. No. 4,960,764.

Another emulsion useful in the topical compositions is a micro-emulsion system. For example, such system comprises from about 9% to about 15% squalane, from about 25% to about 40% silicone oil; from about 8% to about 20% of a fatty alcohol; from about 15% to about 30% of polyoxyethylene sorbitan mono-fatty acid (commercially available under the trade name TWEENS) or other nonionics; and from about 7% to about 20% water.

Liposomal formulations are also useful for the compositions comprising an oligopeptide of the present invention. Such liposomal compositions can be prepared by combining a composition comprising an oligopeptide of the present invention with a phospholipid, such as dipalmitoylphosphatidyl choline, cholesterol and water according to known methods. Epidermal lipids of suitable composition for forming liposomes may be substituted for the phospholipid. The liposome preparation is then incorporated into one of the above topical formulations (for example, a gel or an oil-in-water emulsion) in order to produce the liposome formulation. Other compositions and pharmaceutical uses of topically applied liposomes are described in, for example, Mezei (1985) Topics in Pharmaceutical Sciences, Breimer et al., eds., Elsevier Science, New York, N.Y., pp. 345-358.

The dose of the aforementioned hair growth promoting agent can be selected suitably depending on the purpose of application, the form of the agent, a kind of the active ingredient and the like. For example, it is possible to determine a dose by referring to the dose specifically shown in the Examples of the present specification. For example, the dose of the active ingredient per day per adult is generally within the range of about 1 µg/kg/day to about 10 mg/kg/day, preferably about 10 kg/kg/day to about 1 mg/kg/day.

The practice of the present invention will employ conventional techniques of molecular biology (including recombinant techniques), cell biology, biochemistry, and immunology, which are within the skill of the art. Such techniques are explained fully in the literature, such as, Molecular Cloning: A Laboratory Manual, Second Edition (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Handbook of Experimental Immunology (D, M. Wei & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987 and annual updates); PCR: The Polymerase Chain Reaction (Mullis et al., eds.,

EXAMPLES

The present invention will be explained more specifically by the following Examples. However, the scope of the invention is not limited to these examples.

Example 1

Production of Modified Oligopeptides

Oligopeptides shown in the following amino acid sequences were synthesized by the solid phase method using Fmoc.

```
                                          (SEQ ID NO: 4)
    Ser-Ile-Glu-Gln-Ser-Cys-Ala-Gln-Glu (SEQ ID NO: 5)
    Ser-Ile-Glu-Gln-Ser-Cys-Glu-Gln-Glu (SEQ ID NO: 6)
    Ser-Ile-Glu-Gln-Ser-Cys-Glu-Gln-Glu-Ala
```

Subsequently, each of the synthesized oligopeptides was allowed to react with each of the following modifying reagents in accordance with instructions included with the agents. The reaction was carried out at a molar ratio between the oligopeptide and the modifying reagent of exactly 1:1.

EMCA (N-ε-maleimidecaproic acid): manufactured by Pierce

KMUA (N-κ-maleimideundecanoic acid): manufactured by Pierce

BMPA (N-β-maleimidepropionic acid): manufactured by Pierce

Phenylmaleimide: manufactured by Sigma

Figures 2A, 2B:
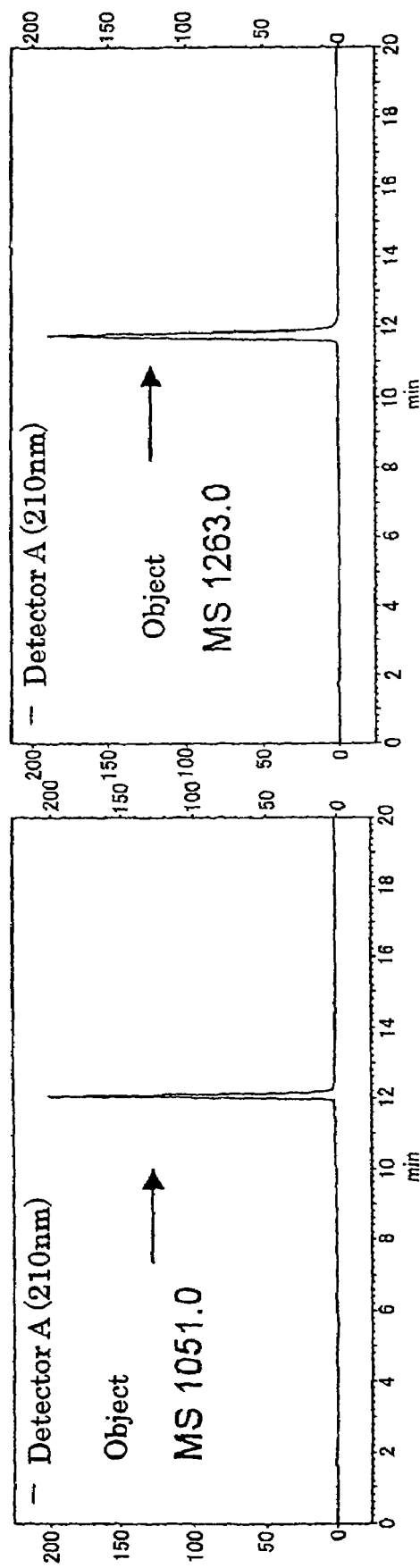
FIGS. 2A-2B show the results obtained by analyzing the synthesized oligopeptide and a reaction product thereof with a modifying reagent by liquid chromatography.

The synthesized oligopeptides and reaction products thereof with the modifying reagents were analyzed by liquid chromatography. The obtained results are shown in FIGS. 1 to 3. The following conditions were applied for liquid chromatography.

Sample to be injected: 20 μl,

Elution condition: TFA, acetonitrile 20%→75%,

The elution position of a peptide is observed at absorption of 210 nm.

In FIGS. 1 to 3, the oligopeptide was allowed to react with the modifying reagent (EMCA) at a molar ratio of exactly 1:1, and a reverse phase liquid chromatogram obtained before and after the reaction is shown.

The left view of FIG. 1 shows the results of the synthesized oligopeptide shown in SEQ ID NO: 1, and the right view of FIG. 1 shows the results of the above oligopeptide, the cysteine residue of which was modified with EMCA.

The left view of FIG. 2 shows the results of the synthesized oligopeptide shown in SEQ ID NO: 2, and the right view of FIG. 2 shows the results of the above oligopeptide, the cysteine residue of which was modified with EMCA.

Figure 3A:
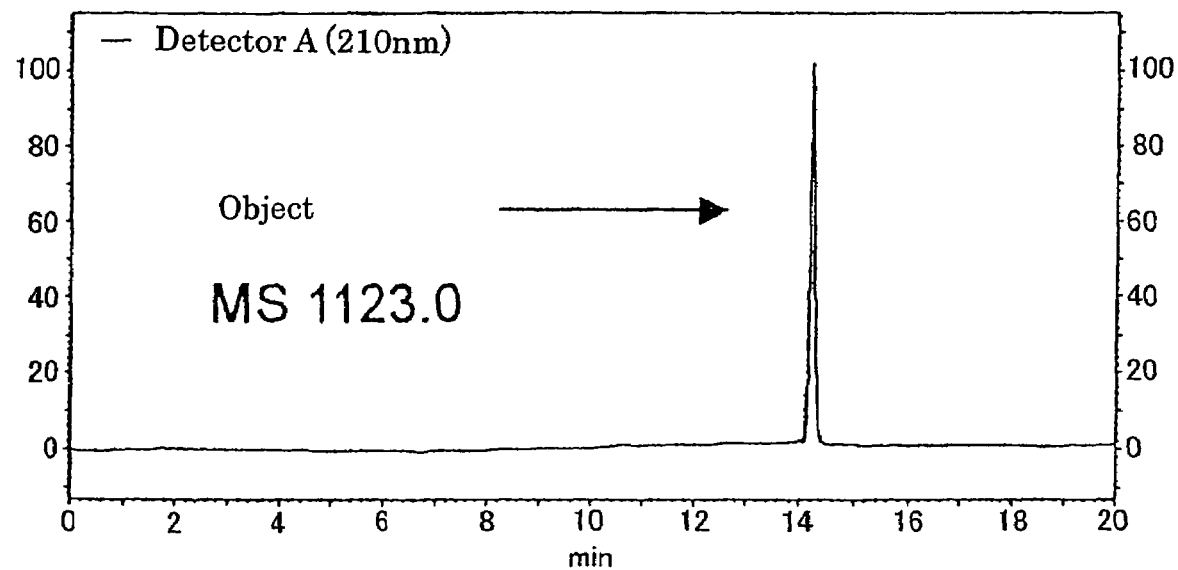
FIGS. 3A-3B show the result obtained by analyzing the synthesized oligopeptide and a reaction product thereof with a modifying reagent of liquid chromatography.
Figure 3B:
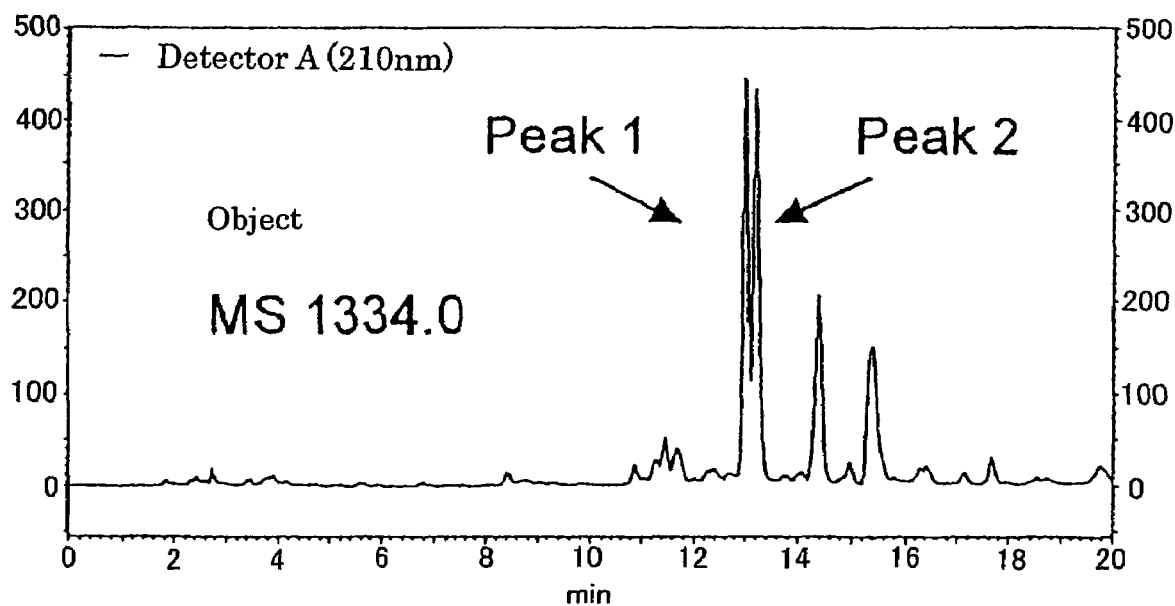

The left view of FIG. 3, FIG. 3A, shows the results of the synthesized oligopeptide shown in SEQ ID NO: 3, and the right view of FIG. 3, FIG. 3B shows the results of the above oligopeptide, the cysteine residue of which was modified with EMCA.

Example 2

Preparation of a Monoclonal Antibody Which is Specific for New Follicle

Hairs were cut off from the skin of B57BL mouse of growing stage (48 to 50 day), and were incubated overnight at 37° C. in PBS containing 8M urea, 2% SDS and 100 mM DTT, thereby the protein was extracted. Further, whisker follicles of B57BL mouse (where hair ball portion is stained with pigment; growing stage) were collected with a stereoscopic microscope, and were homogenized in PBS. The above 2 samples (0.5 mg of protein weight) were mixed, and mixed with the same amount of the complete adjuvant to prepare micelle.

The above-obtained micelle (0.2 mg) was subcutaneously (3 sites) administered to a rat (Wister) for immunization. After the first immunization, the booster was performed in the same way as in the above. After 2 weeks, the second booster was performed in the same way as in the above. On the third day after the second booster, a spleen was removed from the immunized rat, and the blood cells were collected by mesh. Antibody producing cells were contained in these blood cells. All amount of the above-collected blood cells were mixed with mouse myeloma P3U1 using polyethyleneglycol 1500, and were suspended in Dulbecco/Hum F12 mixed medium. 100 μl of the culture were inoculated in each well of 96-well plate. On the next day, the same amount (100 μl) of HAT medium (Sigma) was added to each well. After 2 days, 150 μl of the medium was removed under aspiration from each well, and 150 μl of the fresh medium was added to each well. The 96-well plate was placed in $CO_2$ incubator at 37° C.

The follicles of the growing whisker of B57BL mouse were dissolved in 8M urea by ultrasonic treatment. A nitrocellulose membrane was immersed in this solution for 5 minutes, and was washed well with PBS. Biorad dot blotter equipped with the above membrane was used to perform the first screening of the hybridoma supernatant which was recovered from each well of the above 96-well plate. First, the above prepared nitrocellulose membrane was blocked with Tris buffer containing 5% skim milk (TBST), and then 100 μl of the hybridoma supernatant was added to each well where the nitrocellulose membrane constitutes the bottom. After incubation for 1 hour, the wells were washed with Tris buffer, and the second antibody, horseradish peroxidase labeled anti-rat IgG (1 μg/ml TBST), was added. ECL agent (AmershamPharmacia), which is a coloring substrate, was added, and 50 antibodies in total which reacted with the growing whisker follicle were selected by detection of coloring (first screening).

Among the 50 antibodies selected in the above first screening, the antibodies which specifically reacted with the frozen segment (10 μm) of the growing whisker follicle were selected (second screening). Specifically, the frozen segment of the growing whisker follicle was placed on a slide glass, and the hybridoma supernatant selected in the first screening was added thereto, and the coloring was developed with the second antibody. More specifically, the frozen segment of the growing whisker follicle which was prepared by Cryosdat (Bright) was treated with methanol at −20° C., and was blocked with TBST for 1 hour, and then was reacted with the hybridoma supernatant for 1 hour. The sample was washed with Tris buffer, and was reacted with FITC-labeled anti-rat IgG (100 μg/ml in TBST). The sample was washed with Tris buffer, and was covered with a cover glass. The observation was carried out under fluorescent microscope.

As a result of the second screening, 8 antibodies were selected. These antibodies did not react with epidermis, and specifically reacted with follicle. These 8 antibodies were cloned by the limiting dilution.

The reactivity of these 8 antibodies was examined by Western Blotting using growing whisker follicle (anagen phase) or resting (telogen) whisker follicle as a sample, and using slide samples of the skins having follicles derived from 14 day fetal mouse. As a result, mAb27 was obtained as a monoclonal antibody which specifically reacted with growing whisker follicle and plastic follicle (new follicle), and did not react with resting whisker follicle. The hybridoma which produced monoclonal antibody mAb27 was deposited with Patent and Bio-Resource Center of National Institute of Advanced Industrial Science and Technology (Chuo-6, 1-1, Higashi 1-chome, Tsukuba-shi, Ibaraki-ken, Japan) on Nov. 2, 2001 under the deposit number of FERM P-18578, and was transferred to an international deposition on Jul. 22, 2002 under the deposit number of FERM BP-8121.

Example 3

Evaluation of Hair Growth Promoting Activities of Various Oligopeptides

Various oligopeptides produced in Example 1 were evaluated in terms of hair growth promoting activity. The used oligopeptides are as follows:

```
Ser-Ile-Glu-Gln-Ser-Xaa-Asp,          (SEQ ID NO: 7)
``` wherein Xaa represents the cysteine residue (Cys), to which a modifying group derived from EMCA (N-ε-maleimidecaproic acid), KMUA (N-κ-maleimideundecanoic acid), BMPA (N-β-maleimidepropionic acid) or phenylmaleimide binds,

```
                                      (SEQ ID NO: 8)
Ser-Ile-Glu-Gln-Ser-Xaa-Asp-Gln-Asp-Glu, (SEQ ID NO: 9)
Ser-Ile-Glu-Gln-Ser-Xaa-Ala-Gln-Glu,
and (SEQ ID NO: 10)
Ser-Ile-Glu-Gln-Ser-Xaa-Glu-Gln-Glu,
``` wherein Xaa represents the amino acid residue Cys, to which a modifying group derived from EMCA (N-ε-maleimidecaproic acid) binds.

The skin tissues of the upper jaw of ICR baby mice with an age of 12 days old were recovered under a stereoscopic microscope. The skin tissues were collected from both the left and right sides of the upper jaw, and the tissues were recovered from the total 5 mice. The skin sections recovered from the 5 mice were divided into the skin sections from the left side (used as a control) and those from the right side (used as a test oligopeptide). Thereafter, 5 skin sections were placed on a single nuclepore membrane (pore size: 8 μm; diameter: 13 mm). The skin sections were observed under a stereoscopic microscope, and the outside thereof was disposed on the front. 500 μl of Dulbecco's MEM/Ham F12 medium containing 1% BSA was added to 2 wells of a 24-well dish. Thereafter, a test oligopeptide solution (solvent: PBS) was added to one well to a final concentration of 20 μM, and only a solvent (PBS) as a control was added at the same amount to the other well. As test oligopeptides, unmodified oligopeptides and modified oligopeptides produced in (1) above were used.

Each of the membranes on which the skin tissues were placed was put on the aforementioned solution filled in the well, and it was then cultured at 37° C. for 6 days. From each membrane, 5 tissue sections were recovered in 100 μl of an SDS sample buffer (0.02 g/ml SDS, 0.2 g/ml glycerol, pH 6.8). The recovered sections were then dissolved therein using an ultrasonic crusher. The control was treated in the same manner. The solution obtained by the aforementioned treatment was electrophoresed (35 mA, 1.5 hours) by SDS-PAGE (acrylamide: 4% to 20%), and it was then transferred to a PVDF membrane. Thereafter, it was incubated in a Tris buffer solution (TBST) containing 5% skimmed milk for 1 hour. Thereafter, the resultant was allowed to react with mAb27 (10 μg/ml in TBST) obtained in Example 2 for 1 hour, and it was then sufficiently washed with TBS. Thereafter, peroxidase-labeled anti-rat IgG (Amersham) was 1,000 times diluted with TBST, and the diluted solution was used as a secondary antibody. The secondary antibody was allowed to react with the above resultant product, and the obtained reaction product was then sufficiently washed. Thereafter, the strength of the reaction of mAb27 was examined using an ECL kit (Amersham).

Figure 4:
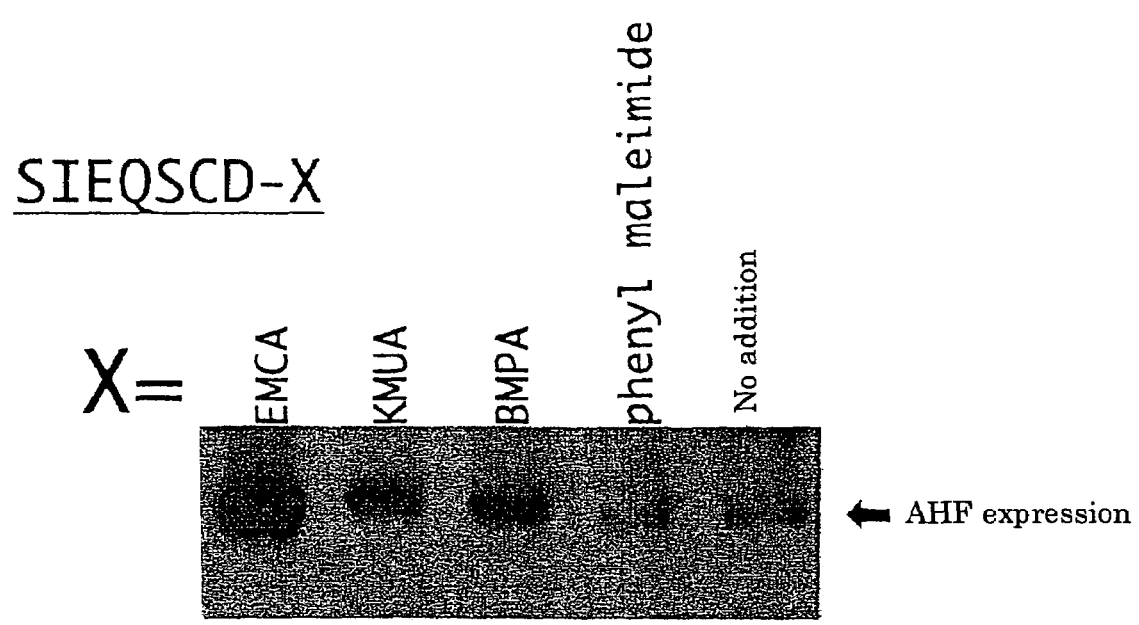
FIG. 4 shows the results obtained by evaluation of the hair growth promoting activities of various oligopeptides.
Figure 5:
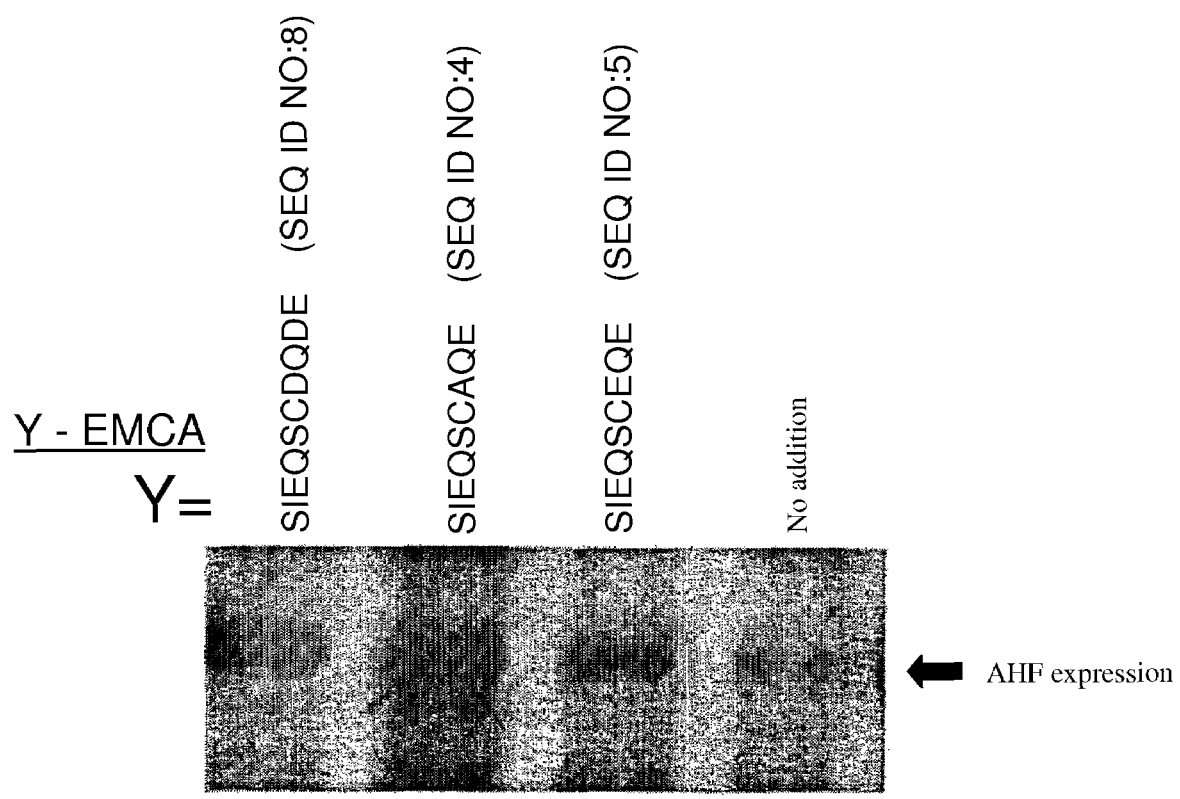
FIG. 5 shows the results obtained by evaluation of the hair growth promoting activities of various oligopeptides.
Figure 6:
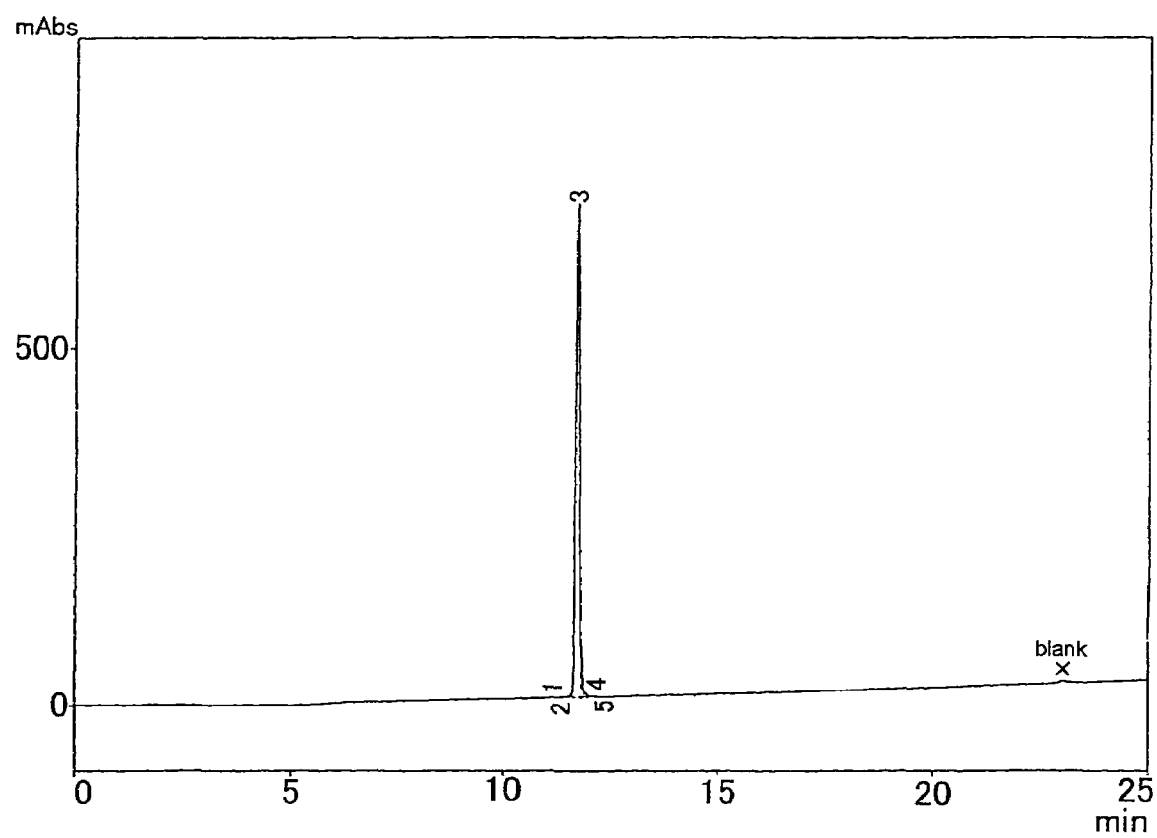
FIG. 6 shows the results obtained by analyzing compound (II) by HPLC.
Figure 7:
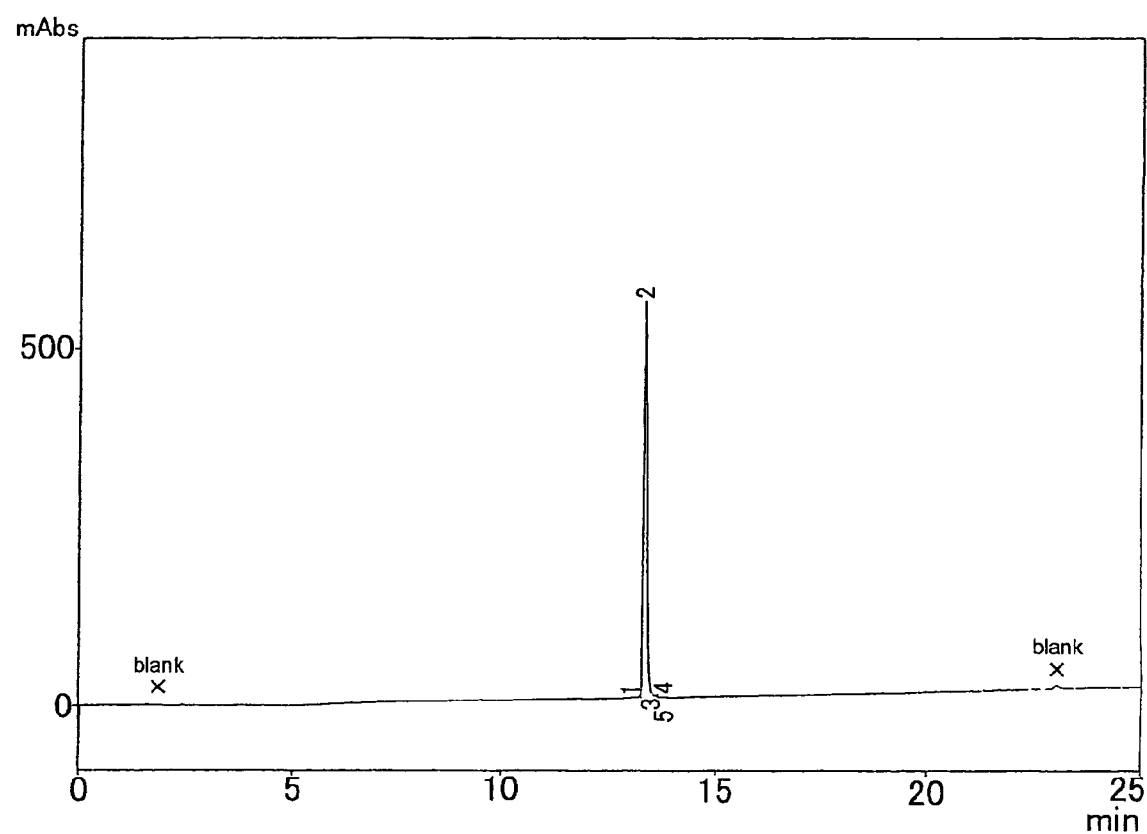
FIG. 7 shows the results obtained by analyzing compound (12) by HPLC.
Figure 8:
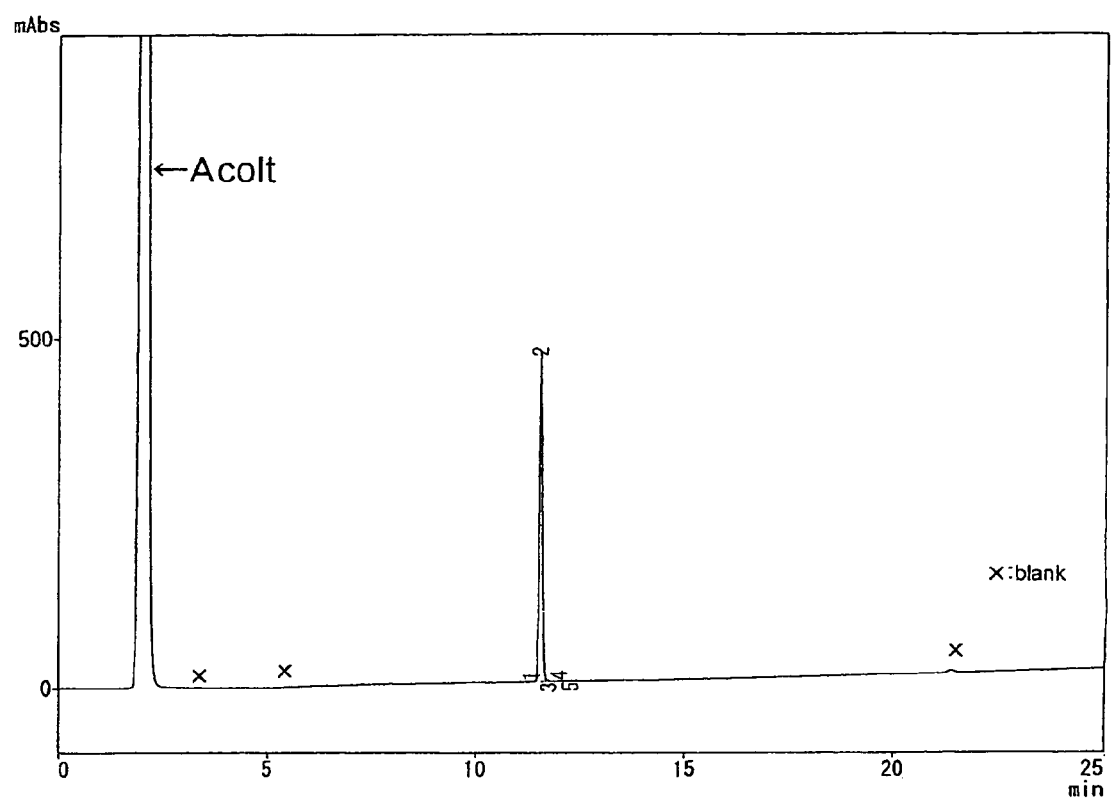
FIG. 8 shows the results obtained by analyzing compound (13) by HPLC.
Figure 9:
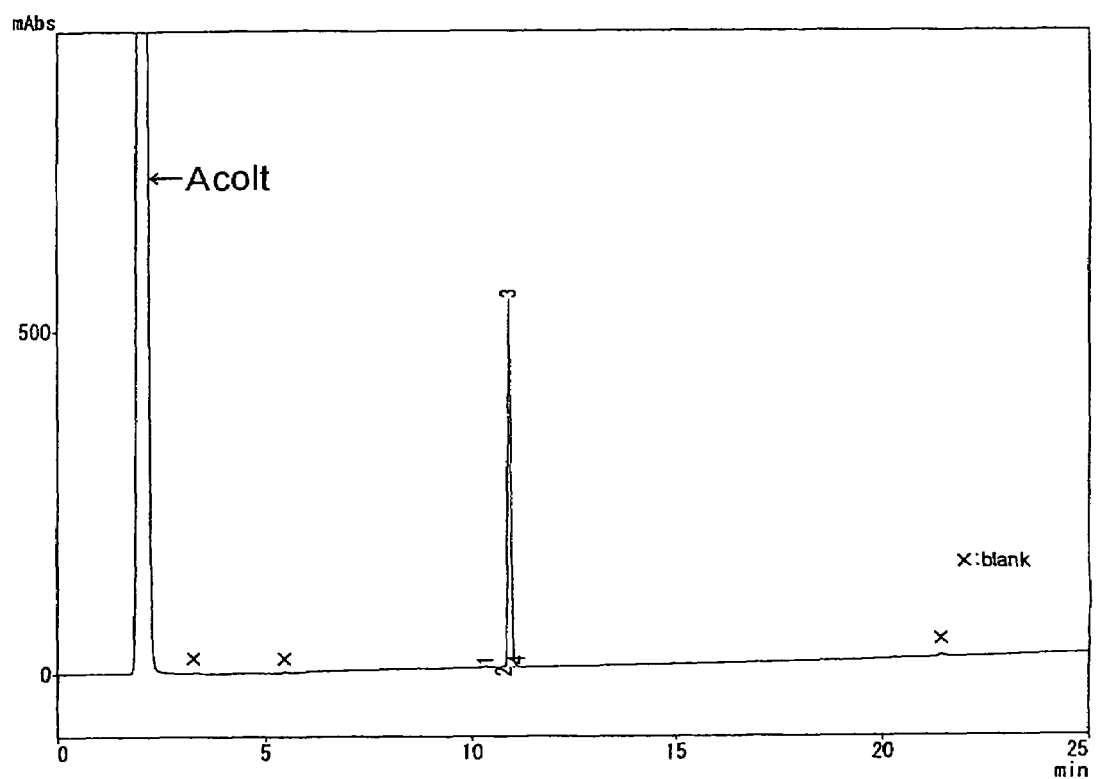
FIG. 9 shows the results obtained by analyzing compound (14) by HPLC.

The obtained results are shown in FIGS. 4 and 5. The term "AHF" shown in FIGS. 4 and 5 represents an antigen recognized by the monoclonal antibody mAb27 (specifically, a protein consisting of 1,439 amino acid residues shown in SEQ ID NO: 11).

As is clear from the results shown in FIG. 4, the bands of the $1^{st}$, $2^{nd}$, and $3^{rd}$ lanes from the left were thicker than those of the $4^{th}$ and $5^{th}$ lanes from the left. These results demonstrate that an oligopeptide, to the cysteine residue of which a modifying group containing a carbonyl group (EMCA, KMUA, or BMPA) binds, has strong hair growth activity, and in particular that the above oligopeptide has stronger hair growth activity than those of the corresponding unmodified oligopeptide or of an oligopeptide to which a modifying group containing no carbonyl groups (phenylmaleimide) binds. Among the aforementioned modifying groups, the activity of EMCA was particularly strong.

In addition, the results shown in FIG. 5 demonstrate that oligopeptides of the following sequences have strong hair growth activity:

```
                                      (SEQ ID NO: 8)
Ser-Ile-Glu-Gln-Ser-Xaa-Asp-Gln-Asp-Glu, (SEQ ID NO: 9)
Ser-Ile-Glu-Gln-Ser-Xaa-Ala-Gln-Glu,
and (SEQ ID NO: 10)
Ser-Ile-Glu-Gln-Ser-Xaa-Glu-Gln-Glu,
``` wherein Xaa represents the amino acid residue Cys, to which a modifying group derived from EMCA (N-ε-maleimidecaproic acid) binds. Among the aforementioned oligopeptides, the oligopeptides of SEQ ID NOS: 8 and 9 exhibited particularly strong hair growth activity.

Example 4

Production of Cyclic Oligopeptides

Cyclic oligopeptides shown in the following amino acid sequences were chemically synthesized. In addition, a compound was synthesized by substituting —CO(CH$_2$)$_5$NH— in compound (11) with —CONH—.

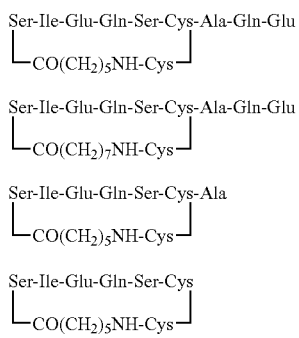

(11) Ser-Ile-Glu-Gln-Ser-Cys-Ala-Gln-Glu
     └─CO(CH₂)₅NH-Cys─┘

(12) Ser-Ile-Glu-Gln-Ser-Cys-Ala-Gln-Glu
     └─CO(CH₂)₇NH-Cys─┘

(13) Ser-Ile-Glu-Gln-Ser-Cys-Ala
     └─CO(CH₂)₅NH-Cys─┘

(14) Ser-Ile-Glu-Gln-Ser-Cys
     └─CO(CH₂)₅NH-Cys─┘

Synthesis was carried out by the following procedures.

Using the peptide automatic synthesizer from Applied Biosystems (430A model, Foster city, Calif., U.S.A.), peptide chains were successively extended from the C-terminus in accordance with the program thereof by the BOC method, so as to synthesize a protective peptide resin of interest. As a starting amino acid resin carrier, Boc-Ala-PAM (0.25 mmol) was used, and common amino acid derivatives such as Cys (MeBzl), Ser (Bzl), or Glu (cHx) were used.

After construction of a peptide on the resin had been completed, the protective peptide resin was dried. The deprotecting group and peptide of the obtained protected peptide were separated from the peptide resin carrier by a treatment with anhydrous hydrogen fluoride. A crude peptide containing a free thiol group was extracted with an aqueous acetic acid solution, and the extract was then freeze-dried, so as to obtain freeze-dried powders. Subsequently, the crude peptide containing a free thiol group was subjected to iodine oxidation in an acetic acid solution, so as to conduct a cyclization reaction, thereby synthesizing the aforementioned cyclic oligopeptide. The obtained crude peptide was subjected to reverse phase high performance chromatography (Shimadzu Corp., preparative device, model LC8A). The crude peptide was isolated and purified using an acetonitrile-0.1% trifluoroacetic acid solution system, so as to obtain a cyclic oligopeptide of interest. The obtained purified product was tested by analytical HPLC, mass spectrometry, and amino acid analysis. The identification data of the compounds as synthesized above are shown below. Moreover, the results of HPLC are shown in FIGS. 6 to 9.

Compound (11)

Appearance: white freeze-dried product

Amino acid analytical value:
  Hydrolysis conditions: 6 N HCl, 110° C., 22 hours
  Ser (2) 1.78, Glu (4) 4.00, Ala (1) 0.96, Ile (1) 0.98, NH₃ (2) 2.05, Cys (2) 1.86, ε-Acp (1) 1.05

Purity (HPLC): 98.4%

ESI-MS: molecular weight 1207.7 (theoretical value: 1208.3)

Compound (12)

Appearance: white freeze-dried product

Amino acid analytical value:
  Hydrolysis conditions: 6 N HCl, 110° C., 22 hours
  Ser (2) 1.80, Glu (4) 4.00, Ala (1) 1.00, Ile (1) 0.99, NH₃ (2) 2.08, Cys (2) 1.91, 8-Aoa (1) N. D. (Since this is not eluted under general analytical conditions, it cannot be quantified.)

Purity (HPLC): 97.8%

ESI-MS: molecular weight 1235.8 (theoretical value: 1236.4)

Compound (13)

Appearance: white freeze-dried product

Amino acid analytical value:
  Hydrolysis conditions: 6 N HCl, 110° C., 22 hours
  Ser (2) 1.79, Glu (2) 2.01, Ala (1) 1.00, Ile (1) 0.97, NH₃ (1) 1.20, Cys (2) 1.94, ε-Acp (1) 1.01

Purity (HPLC): 99.0%

ESI-MS: molecular weight 950.5 (theoretical value: 951.1)

Compound (14)

Appearance: white freeze-dried product

Amino acid analytical value:
  Hydrolysis conditions: 6 N HCl, 110° C., 22 hours
  Ser (2) 1.79, Glu (2) 2.00, Ile (1) 0.97, NH₃ (1) 1.18, Cys (2) 1.92, ε-Acp (1) 1.01

Purity (HPLC): 97.9%

ESI-MS: molecular weight 879.6 (theoretical value: 880.0)

Example 5

Evaluation of Hair Growth Promoting Activities of Various Oligopeptides

Each of the cyclic oligopeptides synthesized in Example 4 was treated with 30% acetonitrile and 0.1% trifluoroacetic acid, and then dried. This cyclic oligopeptide was dissolved in a phosphate buffered saline (PBS), resulting in 0.00002% by weight. Thereafter, an equal volume of 100% ethanol was added to the above solution, so as to prepare a 50% ethanol-PBS solution containing 0.00001% by weight of the cyclic oligopeptide. PBS was used as a control solution.

It has been known that C3H mice and C57BL/6 mice have a resting phase consisting of approximately 50 days from 45 to 95 days after the birth. In addition, the skin color thereof is pink during the resting phase, and then, it becomes grey or black during the growth phase. Thus, their hair cycle can be easily determined. The cyclic oligopeptide of the present invention was administered to such mice, so as to evaluate whether or not transition to the growth phase is promoted by the cyclic oligopeptide. C57BL/6 mice with an age of 7 weeks old (48 to 50 days old, female) were purchased. The hair on the back of each mouse was carefully cut with an electric clipper used for animals, so as not to damage it, and it was then confirmed from the skin color that the hair cycle was in a resting phase. Thereafter, 0.2 ml each of the above prepared cyclic oligopeptide solution (0.00001% by weight) was applied to each mouse in a group consisting of 10 mice, once a day, 5 days a week, up to 38 days after initiation of the experiment. The above cyclic oligopeptide solution was applied using a syringe with no needle.

The mice were observed twice a week. Scores were set in 6 stages depending on the ratio of the hair-regenerated area to the area whose hair had been cut. Multiple persons (2 persons) observed the mice by naked eyes, so as to evaluate them. In addition, the above areas were also photographed. The hair growth score was calculated in the following manner. That is, depending on the ratio of the area whose skin color became grey or black to the area whose hair had been cut, the following scores were set: 0% to 20%:1; 20% to 40%:2; 40% to 60%:3; 60% to 80%:4; and 80% to 100%:5. The sum of the aforementioned scores of each group was defined as a hair growth score. The maximum hair growth score of each group was 50 per judge. Since evaluation was carried out by two judges, the maximum hair growth score became 100.

Figures 10A, 10B:
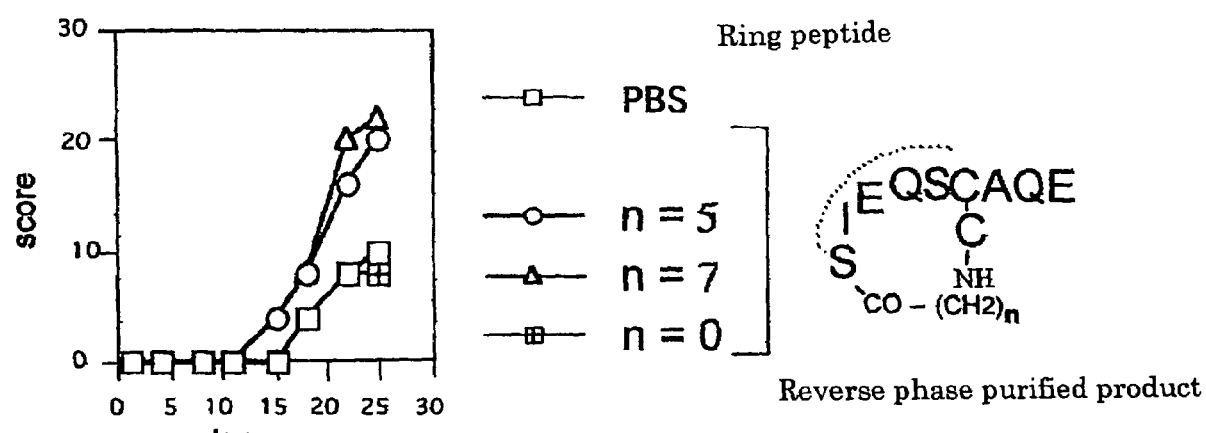
FIGS. 10A-10B show the hair growth promoting activity of the cyclic oligopeptide of the present invention.
Figure 11:
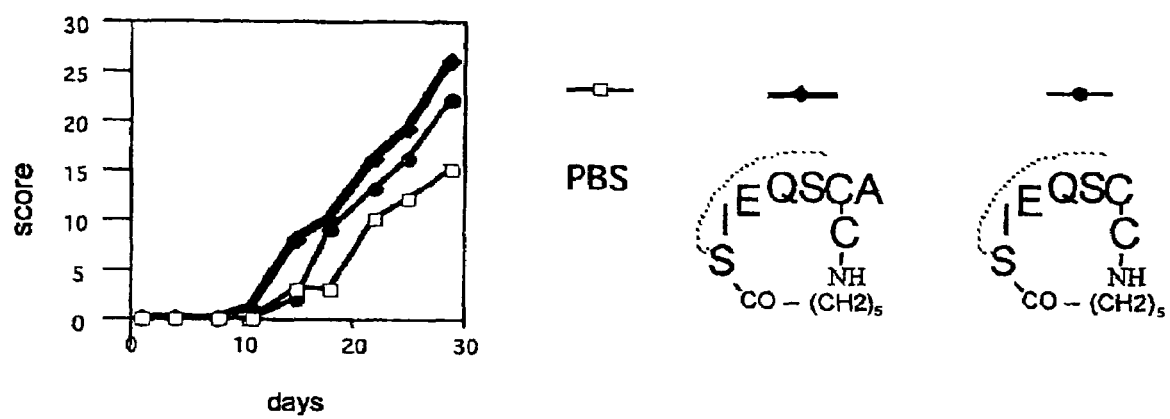
FIG. 11 shows the hair growth promoting activity of the cyclic oligopeptide of the present invention.

Hair regeneration in the group to which the cyclic oligopeptide had been applied was promoted rather than that in the control group. The results are shown in FIGS. 10 and 11. These results demonstrated that the cyclic oligopeptide of the present invention has hair growth promoting activity.

Example 6

Combined Use of the Cyclic Oligopeptide of the Present Invention with Minoxidil

Formulation 1: a mixed solution of the cyclic oligopeptide (0.00001%) represented by formula (13) produced in Example 4 and minoxidil (1%)

Formulation 2: a minoxidil (1%) solution (A commercially available product, "RiUP" (Taisho Pharmaceutical Co., Ltd.) was directly used.)

Figure 12:
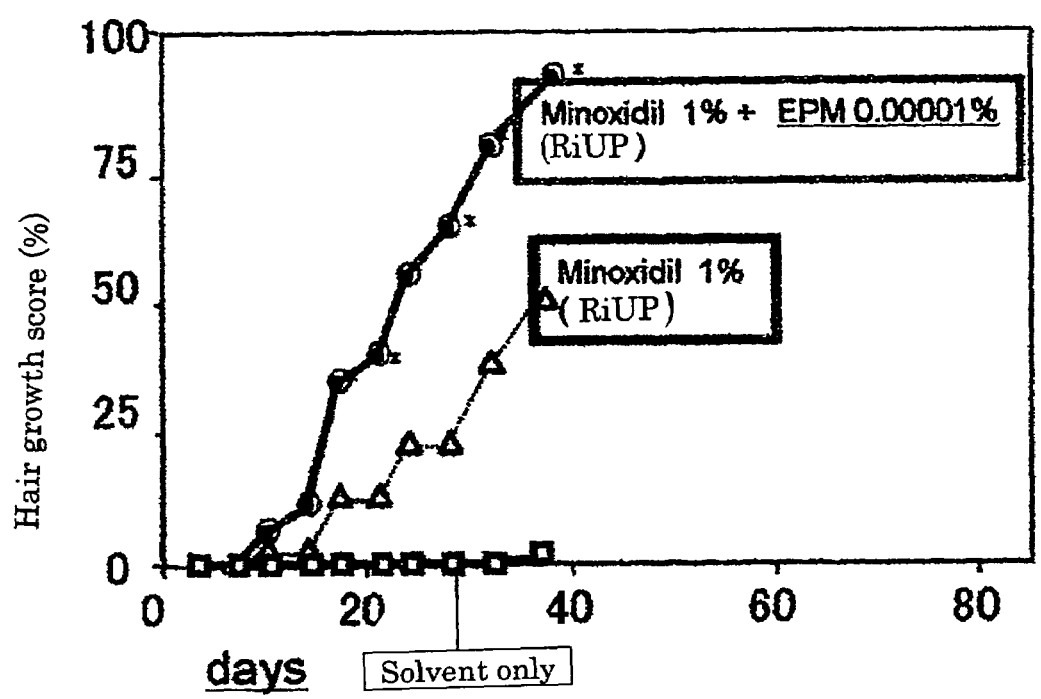
FIG. 12 shows hair growth promoting activity obtained when the cyclic oligopeptide of the present invention was used in combination with minoxidil.

Each of formulation 1 and formulation 2 was administered to the back of a C57BL/6 mouse whose hair follicle was in a resting phase in the same manner as in Example 5, so as to evaluate whether or not the transition of the hair follicle to the growth phase was promoted. The results are shown in FIG. 12. When compared with the case of administration of only minoxidil, in the case of administration of the cyclic peptide of the present invention together with minoxidil, the transition of the hair follicle to the growth phase was drastically promoted. There was a significant difference between both cases at a p-value involving a rejection rate of less than 5% by Wilcoxon test.

Example 7

Evaluation of Cytotoxicity

Each of solutions containing 0.1%, 0.01%, 0.001%, 0.0001%, 0.00001%, and 0.000001% by weight of the cyclic oligopeptide represented by formula (13) produced in Example 4 was subjected to a cytotoxicity test. Skin-derived cells HSC-5 (obtained from Health Science Research Resources Bank, a subordinate organization of Japan Health Sciences Foundation) were used as test cells. The cells were inoculated into a 24-well culture plate at a concentration of 100,000 cells/well. An ISCO V's modified DMEM medium containing 10% FCS was used as a medium. The culture was carried out for 2 days. After completion of the culture, the rate of surviving cells was counted. As a result, the cells survived in all the above cases, and thus no cytotoxicity was observed.

INDUSTRIAL APPLICABILITY

The oligopeptide of the present invention has hair growth promoting activity, and thus it is useful as an active ingredient for a medicament such as a hair growth promoting agent. A specific modifying group is used in the present invention, and as a result, the oligopeptide of the present invention has more improved hair growth promoting activity than that of the peptide described in International Publication WO01/094382. Moreover, the yield can be improved by substituting X7 and X9 with amino acids other than Asp. Furthermore, the cyclic oligopeptide of the present invention has a cyclic structure in a molecule thereof, and it is stable even if it is exposed to an organic solvent. Thus, the present cyclic oligopeptide is stable under strict conditions, such as those for reverse phase chromatography, and it is particularly advantageous in terms of high purification efficiency.

The invention claimed is:

1. A cyclic oligopeptide having the amino acid sequence shown in the following formula (I):

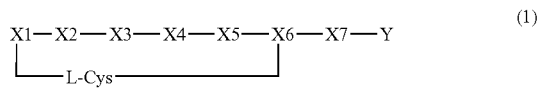

(1)

wherein X1 represent the amino acid residue Ser, X2 represent the amino acid residue Ile, X3 represents the amino acid residue Glu, X4 represents the amino acid residue Gln, X5 represents the amino acid residue Ser, X6 represents the amino acid residue Cys, and X7 represents the amino acid residue Glu or Ala; Y represents an amino acid sequence consisting of 1 to 90 amino acid residues; and L represents a linking group and wherein the cysteine residues are connected through a disulfide bond.

2. The cyclic oligopeptide of claim 1, wherein Y represents an amino acid sequence consisting of 1 to 12 amino acid residues.

3. The cyclic oligopeptide of claim 1, wherein the linking group L contains 6 to 8 carbon atoms.

4. The cyclic oligopeptide of claim 1, wherein a carbonyl group is bound to a hydrocarbon chain containing 5 to 7 carbon atoms in the linking group L.

5. The cyclic oligopeptide of claim 1, wherein the linking group L is CO—$(CH_2)_n$—NH— wherein n represents an integer between 5 and 7.

6. The cyclic oligopeptide of claim 5, wherein —CO in the linking group L is bound to X1, and NH— in the linking group L is bound to the Cys residue binding to X6.

7. The cyclic oligopeptide of claim 1 wherein the cyclic oligopeptide promotes hair growth.

8. A medicament which comprises, as an active ingredient, a cyclic oligopeptide of claim 1, or a physiologically acceptable salt thereof.

9. A cyclic oligopeptide shown in any one of the following sequences:
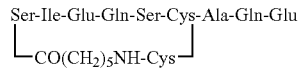
(11)
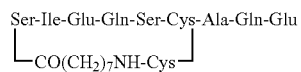
(12)
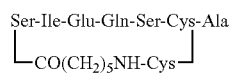
(13)
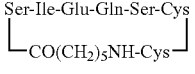
(14)
wherein the cysteine residues are connected through a disulfide bond.
* * * * *

SEQUENCE LISTING

```
<160> NUMBER OF SEQ ID NOS: 14

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 6
<223> OTHER INFORMATION: Xaa = Cys or modified Cys

<400> SEQUENCE: 1

Ser Ile Glu Gln Ser Xaa Ala Gln Glu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
```

```
<222> LOCATION: 6
<223> OTHER INFORMATION: Xaa = Cys or modified Cys

<400> SEQUENCE: 2

Ser Ile Glu Gln Ser Xaa Glu Gln Glu
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 6
<223> OTHER INFORMATION: Xaa = Cys or modified Cys

<400> SEQUENCE: 3

Ser Ile Glu Gln Ser Xaa Glu Gln Glu Ala
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Ser Ile Glu Gln Ser Cys Ala Gln Glu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Ser Ile Glu Gln Ser Cys Glu Gln Glu
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 6

Ser Ile Glu Gln Ser Cys Glu Gln Glu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 6
<223> OTHER INFORMATION: Xaa = Cys or modified Cys

<400> SEQUENCE: 7

Ser Ile Glu Gln Ser Xaa Asp
```

-continued

```
<210> SEQ ID NO 8
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 6
<223> OTHER INFORMATION: Xaa = Cys or modified Cys

<400> SEQUENCE: 8

Ser Ile Glu Gln Ser Xaa Asp Gln Asp Glu
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 6
<223> OTHER INFORMATION: Xaa = Cys or modified Cys

<400> SEQUENCE: 9

Ser Ile Glu Gln Ser Xaa Ala Gln Glu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 6
<223> OTHER INFORMATION: Xaa = Cys or modified Cys

<400> SEQUENCE: 10

Ser Ile Glu Gln Ser Xaa Glu Gln Glu
1               5

<210> SEQ ID NO 11
<211> LENGTH: 1439
<212> TYPE: PRT
<213> ORGANISM: Mus Musculus

<400> SEQUENCE: 11

Met Ser Pro Leu Ile Arg Ser Ile Val Asp Ile Thr Glu Val Phe Asn
1               5                   10                  15

Gln Tyr Ala Ser Gln Ser Cys Asp Gly Ala Ser Leu Ser Lys Lys Asp
            20                  25                  30

Leu Lys Asn Leu Leu Glu Arg Glu Leu Gly Asp Val Leu Gln Arg Pro
        35                  40                  45

His Asp Pro Glu Thr Ile Asp Leu Thr Leu Glu Leu Leu Asp Arg Asp
    50                  55                  60

Cys Asn Gly Arg Val Asp Phe Asn Glu Phe Leu Leu Phe Leu Phe Lys
65                  70                  75                  80

Ile Ala Gln Ala Cys Tyr Tyr Ala Leu Asp Gln Ala Ala Glu Leu Gly
                85                  90                  95
```

-continued

```
Glu Lys Arg Ala Leu Pro Asn Glu Lys Arg Asn Leu Ser Gln Asp Arg
            100                 105                 110

Arg Gln Glu Asp Gln Arg Arg Phe Glu Pro Arg Ser Arg Gln Leu Asp
        115                 120                 125

Glu Glu Pro Gly Arg Arg Ser Trp Gln Lys Arg Glu Gln Glu Glu
    130                 135                 140

Arg Ala Glu Glu Gln Arg Leu Glu Gln Arg Tyr Arg Gln His Arg Asp
145                 150                 155                 160

Glu Glu Gln Arg Leu Gln Arg Arg Glu Leu Gln Glu Leu Glu Glu Arg
                165                 170                 175

Leu Ala Glu Lys Glu Pro Leu Gly Trp Ser Lys Gly Arg Asp Ala Glu
            180                 185                 190

Glu Phe Ser Glu Val Glu Glu Gln Gln Arg Gln Glu Arg Gln Glu Leu
        195                 200                 205

Lys Gly Lys Gly Gln Thr Glu Glu Arg Arg Leu Gln Lys Arg Arg Gln
    210                 215                 220

Glu Glu Leu Arg Glu Pro Leu Leu Arg Arg Asp Leu Glu Leu Arg Arg
225                 230                 235                 240

Glu Gln Glu Leu Arg Arg Glu Gln Glu Leu Arg Gln Glu Gln Arg Arg
                245                 250                 255

Glu Gln Glu Leu Arg Arg Glu Gln Glu Leu Arg Gln Glu Leu Arg Arg
            260                 265                 270

Glu Gln Glu Leu Asn Arg Arg Gln Glu Leu Arg Arg Glu Gln Glu Leu
        275                 280                 285

Arg Arg Glu Gln Glu Leu Arg Gln Glu Leu Arg Arg Glu Gln Glu Leu
    290                 295                 300

Arg Arg Glu Gln Glu Leu Arg Gln Glu Leu Arg Arg Glu Gln Glu Leu
305                 310                 315                 320

Arg Arg Glu Gln Glu Leu Arg Gln Glu Leu Arg Arg Glu Gln Glu Leu
                325                 330                 335

Arg Arg Glu Gln Glu Leu Arg Gln Glu Leu Arg Arg Glu Gln Glu Leu
            340                 345                 350

Arg Arg Glu Gln Glu Leu Arg Gln Glu Leu Ala Glu Glu Asp Glu Leu
        355                 360                 365

Thr Arg Ile Arg Glu Pro Asp Glu Ser Ile Thr Gln Arg Trp Gln Trp
    370                 375                 380

Gln Leu Glu Asn Glu Ala Asp Ala Arg Gln Asn Lys Val Tyr Ser Arg
385                 390                 395                 400

Pro Ser Arg Gln Glu Gln Arg Leu Arg Gln Glu Leu Gly Glu Arg Gln
                405                 410                 415

Leu Arg Glu Gln Glu Glu Gln Arg Arg Asp Leu Gln Gln Glu Arg Pro
            420                 425                 430

Ala Glu Glu Ala Arg Gln Arg Asn Gln Trp Glu Arg Pro Gln Arg Ala
        435                 440                 445

Glu Glu Arg Leu Glu Gln Glu Gln Arg Phe Arg Asp Arg Glu Glu Gln
    450                 455                 460

Arg Phe Arg Glu Glu Lys Leu Gln Arg Ala Glu Leu Gln Asp Ser Leu
465                 470                 475                 480

Leu Asp Glu Glu Gln Arg Arg Leu Gln Glu Arg Arg Glu Pro Asn
                485                 490                 495

Arg Ser Arg Gln Leu Arg Glu Glu Ser Gln Arg Arg Thr Leu Tyr
            500                 505                 510

Ala Lys Pro Ser Gln Arg Gln Gln Arg Arg Arg Leu Gln Gln Glu Arg
```

```
                515                 520                 525
Gln Tyr Gln Glu Glu Asp Leu Gln Arg Leu Arg Asp Glu Asp Gln Arg
    530                 535                 540
Arg Asp Leu Lys Trp Gln Trp Gln Pro Arg Lys Glu Asn Glu Val Arg
545                 550                 555                 560
Ser Asn Arg Leu Phe Thr Lys Arg Arg Gly Asp Glu Glu Pro Ile Gln
            565                 570                 575
Gln Leu Glu Asp Ser Gln Arg Glu Arg Arg Gln Asp Arg Arg Pro
        580                 585                 590
Leu Gln Asp Glu Glu Glu Glu Lys Arg Glu Leu Glu Gln Glu Arg Arg
    595                 600                 605
Arg Arg Gln Gln Arg Asp Arg Gln Ile Leu Glu Glu Glu Gln Phe Gln
    610                 615                 620
Arg Glu His Gln Arg Glu Ala Arg Arg Arg Asp Glu Thr Phe Gln Glu
625                 630                 635                 640
Glu Glu Gln Leu Gln Gly Glu Ser Arg Arg Gln Gln Glu Arg Glu
            645                 650                 655
Gly Lys Phe Leu Glu Glu Arg Gln Leu Arg Thr Glu Arg Glu Glu
        660                 665                 670
Gln Arg Arg Arg Gln Glu Gln Glu Arg Glu Phe Gln Glu Glu Glu Glu
    675                 680                 685
His Leu Gln Glu Arg Glu Lys Glu Leu Arg Gln Glu Cys Asp Arg Lys
    690                 695                 700
Ser Arg Glu Gln Glu Arg Arg Gln Gln Glu Glu Glu Gln Leu Arg
705                 710                 715                 720
Arg Gln Glu Arg Asp Gln Arg Phe Arg Arg Glu Gln Glu Arg His Leu
            725                 730                 735
Glu Arg Glu Glu Glu Gln Leu Arg Asp Arg Pro Ser Arg Arg Glu Gln
        740                 745                 750
Glu Arg His Gln Glu Arg Glu Glu Gln Leu Arg Asp Arg Pro Ser
    755                 760                 765
Arg Arg Glu Gln Glu Arg His Gln Glu Arg Glu Glu Glu Gln Leu Arg
    770                 775                 780
Asp Arg Pro Ser Arg Arg Glu Gln Glu Arg His Gln Glu Arg Glu Glu
785                 790                 795                 800
Glu Gln Leu Arg Asp Arg Pro Phe Arg Arg Glu Gln Glu Arg Leu
            805                 810                 815
Glu Arg Glu Glu Glu Gln Leu Arg Asp Arg Pro Ser Arg Arg Glu Gln
        820                 825                 830
Glu Arg His Gln Glu Arg Glu Glu Gln Leu Arg Asp Arg Pro Ser
    835                 840                 845
Arg Arg Glu Gln Glu Arg Arg Leu Glu Arg Glu Glu Glu Gln Leu Arg
    850                 855                 860
Asp Arg Ser Phe Arg Arg Glu Gln Glu Leu Arg Arg Asp Arg Lys Phe
865                 870                 875                 880
His Glu Glu Glu Arg Arg Glu Glu Leu Glu Glu Glu Gln Arg Gly
            885                 890                 895
Gln Glu Arg Asp Arg Leu Arg Val Glu Glu Gln Leu Arg Gly Gln Arg
        900                 905                 910
Glu Glu Glu Gln Arg Arg Arg Gln Glu Cys Asp Arg Lys Leu His Arg
    915                 920                 925
Glu Leu Glu Val Arg Gln Glu Leu Glu Glu Glu Arg Leu Arg Asp Arg
    930                 935                 940
```

-continued

```
Lys Leu Arg Arg Glu Gln Glu Leu Arg Arg Asp Arg Lys Phe His Glu
945                 950                 955                 960

Glu Glu Glu Arg Arg His Glu Glu Phe Glu Glu Lys Gln Leu Arg Leu
            965                 970                 975

Gln Glu Pro Asp Arg Arg Phe Arg Arg Glu Gln Glu Leu Arg Gln Glu
        980                 985                 990

Cys Val Glu Glu Glu Arg Leu Arg Asp Ser Lys Ile Arg Arg Glu Gln
    995                 1000                1005

Glu Leu Arg Arg Glu Arg Glu Glu Glu Arg Leu Arg Asp Arg Lys Ile
    1010                1015                1020

Arg Arg Asp Gln Glu Leu Arg Gln Gly Leu Glu Glu Glu Gln Leu Arg
1025                1030                1035                1040

Arg Gln Glu Leu Asp Arg Lys Phe Arg Glu Glu Gln Glu Leu Asp Gln
            1045                1050                1055

Glu Leu Glu Glu Glu Arg Leu Arg Asp Arg Lys Ile Arg Arg Glu Gln
        1060                1065                1070

Glu Leu Arg Arg Glu Gln Glu Leu Arg Arg Glu Gln Glu Phe Arg Arg
    1075                1080                1085

Glu Gln Glu Leu Arg Arg Glu Gln Glu Phe Arg Arg Glu Gln Glu Leu
    1090                1095                1100

Arg Gln Glu Arg Glu Glu Glu Arg Leu Arg Asp Arg Lys Ile Arg Arg
1105                1110                1115                1120

Asp Gln Glu Leu Arg Gln Gly Leu Glu Glu Glu Gln Leu Arg Arg Gln
            1125                1130                1135

Glu Arg Asp Arg Lys Phe Arg Glu Glu Gln Glu Leu Gly Gln Glu Leu
        1140                1145                1150

Glu Glu Glu Arg Leu Arg Asp Arg Lys Ile Arg Arg Glu Gln Glu Leu
    1155                1160                1165

Arg Arg Glu Arg Glu Gln Glu Gln Arg Arg Arg Leu Glu Arg Glu Glu
    1170                1175                1180

Glu Gln Gln Arg Leu His Glu Arg Glu Glu Glu Gln Arg Arg Arg Gln
1185                1190                1195                1200

Glu Arg Glu Gln Glu Gln Gln Arg Cys Leu Glu Arg Glu Glu Glu Gln
            1205                1210                1215

Phe Arg Phe Glu Glu Gln Gln Arg Arg Arg Gln Glu Arg Glu Gln Gln
        1220                1225                1230

Leu Arg Gln Glu Arg Asp Arg Arg Val Leu Glu Glu Glu Glu Leu Arg
    1235                1240                1245

Gln Glu Arg Glu Glu Leu Leu His Arg Gln Val Gly Gly Arg Lys Phe
    1250                1255                1260

Arg Glu Glu Glu Arg Leu Arg Leu Glu Arg Glu Glu Gln Gln Arg Arg
1265                1270                1275                1280

Leu Gln Glu Arg Asp Asn Arg Arg Phe Arg Glu Glu Val Glu Leu Arg
            1285                1290                1295

Gln Glu Arg Glu Gly Gln Gln Leu Arg Gln Glu Arg Asp Arg Lys Phe
        1300                1305                1310

Arg Glu Val Glu Glu Leu Arg Gln Glu Glu Gln Arg Arg Arg Gln Glu
    1315                1320                1325

Arg Asp Arg Lys Phe Arg Glu Glu Lys His Pro Arg Glu Glu Arg Glu
    1330                1335                1340

Glu Gln Gln Leu Arg Arg Glu Lys Arg Asp Gly Gln Tyr Leu Ala Glu
1345                1350                1355                1360
```

```
Glu Gln Phe Ala Arg Asp Thr Ile Arg Arg Gln Gln Glu Leu Arg
            1365                1370                1375

Gln Glu Glu Glu Gln Arg Arg Arg Gln Glu Arg Glu Arg Lys Phe Gln
        1380                1385                1390

Glu Glu Gln Ile Arg Arg Arg Gln Glu Glu Gln Arg Arg Arg Gln Ile
        1395                1400                1405

Leu Glu Pro Gly Thr Arg Gln Phe Ala Asn Val Pro Val Arg Ser Ser
    1410                1415                1420

Pro Leu Tyr Glu Tyr Ile Gln Glu Gln Arg Ser Gln Tyr Arg Pro
1425                1430                1435

<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 12

Ser Ile Glu Gln Ser Cys Ala Gln Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 13

Ser Ile Glu Gln Ser Cys Ala
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 14

Ser Ile Glu Gln Ser Cys
1               5
```